(12) United States Patent
Burbank

(10) Patent No.: US 11,642,129 B2
(45) Date of Patent: May 9, 2023

(54) STAPLE CARTRIDGE AND DRIVE MEMBER FOR SURGICAL INSTRUMENT

(71) Applicant: INTUITIVE SURGICAL OPERATIONS, INC., Sunnyvale, CA (US)

(72) Inventor: William Burbank, Sandy Hook, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 19 days.

(21) Appl. No.: 17/147,435

(22) Filed: Jan. 12, 2021

(65) Prior Publication Data
US 2021/0212683 A1 Jul. 15, 2021

Related U.S. Application Data

(60) Provisional application No. 62/961,504, filed on Jan. 15, 2020.

(51) Int. Cl.
*A61B 17/072* (2006.01)
*A61B 17/10* (2006.01)
*A61B 17/00* (2006.01)

(52) U.S. Cl.
CPC ........ *A61B 17/07207* (2013.01); *A61B 17/10* (2013.01); *A61B 2017/00367* (2013.01);
(Continued)

(58) Field of Classification Search
CPC .................... A61B 2017/07271; A61B 17/068
(Continued)

(56) References Cited

U.S. PATENT DOCUMENTS 4,305,539 A 12/1981 Korolkov et al.
4,319,576 A 3/1982 Rothfuss
(Continued)

FOREIGN PATENT DOCUMENTS

EP 0277532 B1 8/1990
EP 0277529 B1 4/1993
(Continued)

OTHER PUBLICATIONS

International Preliminary Report on Patentability for Application No. PCT/US2019/017646, dated Aug. 27, 2020, 10 pages.
(Continued)

*Primary Examiner* — Michelle Lopez
(74) *Attorney, Agent, or Firm* — Farber LLC

(57) ABSTRACT

The present disclosure provides a surgical instrument, such as a tissue sealing instrument, having a staple cartridge with a staple pusher and a staple; and a drive member configured to translate distally through the instrument. The drive member includes a lateral projection configured to engage the staple pusher and drive the staple into tissue. The lateral projection of the drive member has a height substantially less than the height of the staple cartridge, thereby requiring less clearance as it translates through the staple cartridge. In addition, the lateral projection has a smaller footprint than conventional drive members resulting in a more compact distal tip on the staple cartridge, which allows for a more compact and maneuverable surgical instrument.

17 Claims, 16 Drawing Sheets

(52) U.S. Cl.
CPC .............. *A61B 2017/07264* (2013.01); *A61B 2017/07271* (2013.01)

(58) Field of Classification Search
USPC .................................................... 227/175.1
See application file for complete search history.

(56) References Cited

U.S. PATENT DOCUMENTS

| | | |
|---|---|---|
| 4,429,695 A | 2/1984 | Green |
| 4,509,518 A | 4/1985 | McGarry et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,767,044 A | 8/1988 | Green |
| 4,809,695 A | 3/1989 | Gwathmey et al. |
| 4,848,637 A | 7/1989 | Pruitt |
| 4,892,244 A | 1/1990 | Fox et al. |
| 4,930,503 A | 6/1990 | Pruitt |
| 4,978,049 A | 12/1990 | Green |
| 5,027,834 A | 7/1991 | Pruitt |
| 5,040,715 A | 8/1991 | Green et al. |
| 5,133,735 A | 7/1992 | Slater et al. |
| 5,133,736 A | 7/1992 | Bales, Jr. et al. |
| 5,180,092 A | 1/1993 | Crainich |
| 5,275,323 A | 1/1994 | Schulze et al. |
| 5,307,976 A | 5/1994 | Olson et al. |
| 5,312,023 A | 5/1994 | Green et al. |
| 5,334,183 A | 8/1994 | Wuchinich |
| 5,342,396 A | 8/1994 | Cook |
| 5,366,133 A | 11/1994 | Geiste |
| 5,452,836 A | 9/1995 | Huitema et al. |
| 5,452,837 A | 9/1995 | Williamson, IV et al. |
| 5,480,089 A | 1/1996 | Blewett |
| 5,484,095 A | 1/1996 | Green et al. |
| 5,484,451 A | 1/1996 | Akopov et al. |
| 5,487,500 A | 1/1996 | Knodel et al. |
| 5,497,931 A | 3/1996 | Nakamura |
| 5,533,521 A | 7/1996 | Granger |
| 5,540,375 A | 7/1996 | Bolanos et al. |
| 5,554,164 A | 9/1996 | Wilson et al. |
| 5,560,530 A | 10/1996 | Bolanos et al. |
| 5,562,239 A | 10/1996 | Boiarski et al. |
| 5,571,116 A | 11/1996 | Bolanos et al. |
| 5,571,285 A | 11/1996 | Chow et al. |
| 5,573,534 A | 11/1996 | Stone |
| 5,615,820 A | 4/1997 | Viola |
| 5,624,452 A | 4/1997 | Yates |
| 5,628,446 A | 5/1997 | Geiste et al. |
| 5,652,849 A | 7/1997 | Conway et al. |
| 5,667,626 A | 9/1997 | Cayford et al. |
| 5,676,674 A | 10/1997 | Bolanos et al. |
| 5,688,269 A | 11/1997 | Newton et al. |
| 5,690,269 A | 11/1997 | Bolanos et al. |
| 5,693,042 A | 12/1997 | Boiarski et al. |
| 5,697,542 A | 12/1997 | Knodel et al. |
| 5,709,680 A | 1/1998 | Yates et al. |
| 5,752,644 A | 5/1998 | Bolanos et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,792,135 A | 8/1998 | Madhani et al. |
| 5,820,009 A | 10/1998 | Melling et al. |
| 5,826,776 A | 10/1998 | Schulze et al. |
| 5,833,695 A | 11/1998 | Yoon |
| 5,865,361 A | 2/1999 | Milliman et al. |
| 5,871,135 A | 2/1999 | Williamson, IV et al. |
| 5,911,353 A | 6/1999 | Bolanos et al. |
| 5,915,616 A | 6/1999 | Viola et al. |
| 5,941,442 A | 8/1999 | Geiste et al. |
| 5,954,259 A | 9/1999 | Viola et al. |
| 5,959,892 A | 9/1999 | Lin et al. |
| 6,032,849 A | 3/2000 | Mastri et al. |
| 6,079,606 A | 6/2000 | Milliman et al. |
| 6,174,309 B1 | 1/2001 | Wrublewski et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,330,956 B1 | 12/2001 | Willinger |
| 6,330,965 B1 | 12/2001 | Milliman et al. |
| 6,488,196 B1 * | 12/2002 | Fenton, Jr. ........... A61B 17/068 227/176.1 |
| 6,503,259 B2 | 1/2003 | Huxel et al. |
| 6,585,735 B1 | 7/2003 | Frazier et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,786,382 B1 | 9/2004 | Hoffman |
| 6,817,974 B2 | 11/2004 | Cooper et al. |
| 6,877,647 B2 | 4/2005 | Green et al. |
| 6,905,057 B2 | 6/2005 | Swayze et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,114,642 B2 | 10/2006 | Whitman |
| 7,128,253 B2 | 10/2006 | Mastri et al. |
| 7,140,527 B2 | 11/2006 | Ehrenfels et al. |
| 7,140,528 B2 | 11/2006 | Shelton, IV et al. |
| 7,258,262 B2 | 8/2007 | Mastri et al. |
| 7,308,998 B2 | 12/2007 | Mastri et al. |
| 7,328,828 B2 | 2/2008 | Ortiz et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,401,721 B2 | 7/2008 | Holsten et al. |
| 7,407,075 B2 | 8/2008 | Holsten et al. |
| 7,455,676 B2 | 11/2008 | Holsten et al. |
| 7,472,814 B2 | 1/2009 | Mastri et al. |
| 7,481,349 B2 | 1/2009 | Holsten et al. |
| 7,494,039 B2 | 2/2009 | Racenet et al. |
| 7,565,993 B2 | 7/2009 | Milliman et al. |
| 7,588,174 B2 | 9/2009 | Holsten et al. |
| 7,673,783 B2 | 3/2010 | Morgan et al. |
| 7,699,835 B2 | 4/2010 | Lee et al. |
| 7,721,930 B2 | 5/2010 | McKenna et al. |
| 7,726,539 B2 | 6/2010 | Holsten et al. |
| 7,770,774 B2 | 8/2010 | Mastri et al. |
| 7,832,611 B2 | 11/2010 | Boyden et al. |
| 7,837,079 B2 | 11/2010 | Holsten et al. |
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten et al. |
| 8,083,118 B2 | 12/2011 | Milliman et al. |
| 8,127,975 B2 | 3/2012 | Olson et al. |
| 8,157,152 B2 | 4/2012 | Holsten et al. |
| 8,272,553 B2 | 9/2012 | Mastri et al. |
| 8,308,042 B2 | 11/2012 | Aranyi |
| 8,348,127 B2 * | 1/2013 | Marczyk ........... A61B 17/07207 227/179.1 |
| 8,365,972 B2 | 2/2013 | Aranyi et al. |
| 8,371,492 B2 | 2/2013 | Aranyi et al. |
| 8,551,091 B2 | 10/2013 | Couture et al. |
| 8,573,465 B2 | 11/2013 | Shelton, IV |
| 8,579,178 B2 | 11/2013 | Holsten et al. |
| 8,608,047 B2 | 12/2013 | Holsten et al. |
| 8,672,939 B2 | 3/2014 | Garrison |
| 8,783,541 B2 | 7/2014 | Shelton, IV et al. |
| 8,800,841 B2 | 8/2014 | Ellerhorst et al. |
| 8,858,547 B2 | 10/2014 | Brogna |
| 8,905,287 B2 | 12/2014 | Racenet et al. |
| 8,925,785 B2 | 1/2015 | Holsten et al. |
| 9,010,606 B2 | 4/2015 | Aranyi et al. |

(56) References Cited

U.S. PATENT DOCUMENTS

| | | |
|---|---|---|
| 9,055,961 B2 | 6/2015 | Manzo et al. |
| 9,192,378 B2 | 11/2015 | Aranyi et al. |
| 9,192,379 B2 | 11/2015 | Aranyi et al. |
| 9,216,019 B2 | 12/2015 | Schmid et al. |
| 9,345,479 B2 | 5/2016 | Racenet et al. |
| 9,717,497 B2 | 8/2017 | Zerkle et al. |
| 9,717,498 B2 | 8/2017 | Aranyi et al. |
| 9,936,949 B2 * | 4/2018 | Measamer ......... A61B 17/1155 |
| 10,111,659 B2 | 10/2018 | Racenet et al. |
| 10,231,732 B1 | 3/2019 | Racenet et al. |
| 10,285,693 B2 | 5/2019 | Kimsey et al. |
| 10,646,219 B2 | 5/2020 | Racenet et al. |
| 10,828,027 B2 | 11/2020 | Racenet et al. |
| 10,863,988 B2 | 12/2020 | Patel et al. |
| 11,439,390 B2 | 9/2022 | Patel et al. |
| 11,504,124 B2 | 11/2022 | Patel et al. |
| 2002/0165562 A1 | 11/2002 | Grant et al. |
| 2003/0181910 A1 | 9/2003 | Dycus et al. |
| 2004/0232199 A1 | 11/2004 | Shelton et al. |
| 2004/0267310 A1 | 12/2004 | Racenet et al. |
| 2005/0006430 A1 | 1/2005 | Wales |
| 2005/0006434 A1 | 1/2005 | Wales et al. |
| 2005/0070925 A1 | 3/2005 | Shelton, IV et al. |
| 2005/0070958 A1 | 3/2005 | Swayze et al. |
| 2005/0113826 A1 | 5/2005 | Johnson et al. |
| 2005/0173490 A1 | 8/2005 | Shelton, IV |
| 2005/0178813 A1 | 8/2005 | Swayze et al. |
| 2005/0187576 A1 | 8/2005 | Whitman et al. |
| 2006/0000868 A1 | 1/2006 | Shelton, IV et al. |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0024817 A1 | 2/2006 | Deguchi et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton, IV |
| 2006/0049230 A1 | 3/2006 | Shelton, IV et al. |
| 2006/0097026 A1 | 5/2006 | Shelton, IV |
| 2006/0161190 A1 | 7/2006 | Gadberry et al. |
| 2006/0190031 A1 | 8/2006 | Wales et al. |
| 2006/0226196 A1 | 10/2006 | Hueil et al. |
| 2007/0010838 A1 | 1/2007 | Shelton, IV et al. |
| 2007/0045379 A1 | 3/2007 | Shelton, IV |
| 2007/0262116 A1 | 11/2007 | Hueil et al. |
| 2008/0023522 A1 | 1/2008 | Olson et al. |
| 2008/0078804 A1 | 4/2008 | Shelton et al. |
| 2009/0277947 A1 | 11/2009 | Viola |
| 2010/0108740 A1 | 5/2010 | Pastorelli et al. |
| 2010/0145334 A1 | 6/2010 | Olson et al. |
| 2010/0179545 A1 | 7/2010 | Twomey et al. |
| 2011/0022078 A1 | 1/2011 | Hinman |
| 2011/0174863 A1 | 7/2011 | Shelton, IV et al. |
| 2011/0251612 A1 | 10/2011 | Faller et al. |
| 2011/0251613 A1 | 10/2011 | Guerra et al. |
| 2011/0290854 A1 * | 12/2011 | Timm .............. A61B 17/07207 227/178.1 |
| 2011/0295270 A1 | 12/2011 | Giordano et al. |
| 2012/0022584 A1 | 1/2012 | Donnigan et al. |
| 2012/0071891 A1 | 3/2012 | Itkowitz et al. |
| 2012/0223121 A1 | 9/2012 | Viola et al. |
| 2013/0015231 A1 | 1/2013 | Kostrzewski |
| 2013/0056521 A1 | 3/2013 | Swensgard |
| 2013/0068821 A1 | 3/2013 | Huitema et al. |
| 2013/0087599 A1 | 4/2013 | Krumanaker et al. |
| 2013/0098965 A1 | 4/2013 | Kostrzewski et al. |
| 2013/0148577 A1 | 6/2013 | Terry et al. |
| 2013/0248577 A1 | 9/2013 | Leimbach et al. |
| 2013/0296922 A1 | 11/2013 | Allen, IV et al. |
| 2014/0001236 A1 | 1/2014 | Shelton, IV et al. |
| 2014/0025071 A1 | 1/2014 | Sims et al. |
| 2014/0175152 A1 | 6/2014 | Hess et al. |
| 2014/0180286 A1 | 6/2014 | Marczyk et al. |
| 2014/0263546 A1 | 9/2014 | Aranyi |
| 2014/0263559 A1 | 9/2014 | Williams et al. |
| 2014/0263567 A1 | 9/2014 | Williams et al. |
| 2014/0263569 A1 | 9/2014 | Williams et al. |
| 2014/0343550 A1 | 11/2014 | Faller et al. |
| 2014/0364851 A1 | 12/2014 | Batross et al. |
| 2015/0209037 A1 | 7/2015 | Kostrzewski et al. |
| 2015/0250530 A1 | 9/2015 | Manzo et al. |
| 2015/0256609 A1 | 9/2015 | Morton et al. |
| 2015/0272576 A1 | 10/2015 | Cappola |
| 2015/0297227 A1 | 10/2015 | Huitema et al. |
| 2016/0038227 A1 | 2/2016 | Garrison |
| 2016/0120544 A1 | 5/2016 | Shelton, IV et al. |
| 2016/0175033 A1 | 6/2016 | Le |
| 2016/0192999 A1 | 7/2016 | Stulen et al. |
| 2016/0235489 A1 | 8/2016 | Gombert et al. |
| 2016/0270780 A1 | 9/2016 | Hall et al. |
| 2016/0287251 A1 | 10/2016 | Shelton, IV et al. |
| 2016/0338764 A1 | 11/2016 | Krastins et al. |
| 2017/0010578 A1 | 1/2017 | Miyakawa |
| 2017/0042604 A1 | 2/2017 | McFarland et al. |
| 2017/0079710 A1 | 3/2017 | Deville et al. |
| 2017/0097035 A1 | 4/2017 | Zimmerman et al. |
| 2017/0135746 A1 | 5/2017 | Tetzlaff et al. |
| 2017/0189028 A1 | 7/2017 | Aranyi |
| 2017/0245857 A1 | 8/2017 | Shelton, IV et al. |
| 2017/0296172 A1 | 10/2017 | Harris et al. |
| 2018/0021042 A1 | 1/2018 | Nicholas et al. |
| 2018/0161052 A1 | 6/2018 | Weir et al. |
| 2018/0168581 A1 | 6/2018 | Hunter et al. |
| 2018/0168622 A1 | 6/2018 | Shelton, IV et al. |
| 2018/0168628 A1 | 6/2018 | Hunter et al. |
| 2018/0168641 A1 | 6/2018 | Harris et al. |
| 2018/0168642 A1 | 6/2018 | Shelton, IV et al. |
| 2018/0168649 A1 | 6/2018 | Shelton, IV et al. |
| 2018/0232951 A1 | 8/2018 | Alterovitz et al. |
| 2018/0310948 A1 | 11/2018 | Stamm et al. |
| 2019/0000454 A1 | 1/2019 | Swayze et al. |
| 2019/0015124 A1 | 1/2019 | Williams et al. |
| 2019/0125347 A1 | 5/2019 | Stokes et al. |
| 2019/0142531 A1 | 5/2019 | Wentworth et al. |
| 2019/0167266 A1 | 6/2019 | Patel et al. |
| 2019/0231350 A1 | 8/2019 | Scott et al. |
| 2019/0290374 A1 | 9/2019 | Ramadorai |
| 2019/0365458 A1 | 12/2019 | Whitlock et al. |
| 2020/0397430 A1 | 12/2020 | Patel et al. |
| 2021/0000557 A1 | 1/2021 | Mustufa et al. |
| 2021/0022736 A1 | 1/2021 | Wixey |
| 2021/0077101 A1 | 3/2021 | Patel et al. |
| 2021/0177495 A1 | 6/2021 | Ross et al. |
| 2021/0177500 A1 | 6/2021 | Khalaji |
| 2021/0386427 A1 | 12/2021 | Millman et al. |
| 2022/0015762 A1 | 1/2022 | Wixey et al. |
| 2022/0015763 A1 | 1/2022 | Wixey et al. |
| 2022/0015823 A1 | 1/2022 | Wilson et al. |
| 2022/0054130 A1 | 2/2022 | Overmyer et al. |
| 2022/0061836 A1 | 3/2022 | Parihar et al. |
| 2022/0061840 A1 | 3/2022 | Hites |
| 2022/0061841 A1 | 3/2022 | Wixey et al. |
| 2022/0071632 A1 | 3/2022 | Patel et al. |
| 2022/0079585 A1 | 3/2022 | Egan |
| 2022/0160358 A1 | 5/2022 | Wixey |
| 2022/0183686 A1 | 6/2022 | Wixey et al. |
| 2022/0192665 A1 | 6/2022 | Wellman |
| 2022/0346790 A1 | 11/2022 | Wellman |

FOREIGN PATENT DOCUMENTS

| | | |
|---|---|---|
| EP | 0641546 A1 | 3/1995 |
| EP | 1090592 A1 | 4/2001 |
| EP | 1728473 A1 | 12/2006 |
| EP | 1479346 B1 | 1/2007 |
| EP | 1621141 B1 | 7/2007 |
| EP | 1316290 B1 | 2/2012 |
| EP | 1754445 B1 | 10/2013 |
| EP | 313522 A2 | 3/2017 |
| EP | 3158947 A1 | 4/2017 |
| EP | 3173029 A1 | 5/2017 |
| FR | 2828952 B1 | 12/2005 |

(56) References Cited

FOREIGN PATENT DOCUMENTS

| | | |
|---|---|---|
| JP | 5301166 B2 | 9/2013 |
| JP | 2014530653 A | 11/2014 |
| JP | 2016508792 A | 3/2016 |
| JP | 2016513570 A | 5/2016 |
| JP | 2017500146 A | 1/2017 |
| JP | 2017513564 A | 6/2017 |
| JP | 2017527396 A | 9/2017 |
| JP | 6411461 B2 | 10/2018 |
| JP | 2019141659 A | 8/2019 |
| SU | 405234 A1 | 9/1975 |
| SU | 886900 A1 | 12/1981 |
| SU | 1333319 A2 | 8/1987 |
| SU | 1442191 A1 | 12/1988 |
| SU | 1459659 A1 | 2/1989 |
| WO | WO-8602254 A1 | 4/1986 |
| WO | WO-9005489 A1 | 5/1990 |
| WO | WO-9734533 A1 | 9/1997 |
| WO | WO-03094743 A1 | 11/2003 |
| WO | WO-03094746 A1 | 11/2003 |
| WO | WO-03094747 A1 | 11/2003 |
| WO | WO-2012142872 A1 | 10/2012 |
| WO | WO-2014106275 A1 | 7/2014 |
| WO | WO-2017026141 A1 | 2/2017 |
| WO | WO-2017034803 A2 | 3/2017 |
| WO | WO-2017156070 A1 | 9/2017 |
| WO | WO-2017214243 A1 | 12/2017 |
| WO | WO-2016005750 A1 | 1/2018 |
| WO | WO-2018071497 A1 | 4/2018 |
| WO | WO-2018118402 A1 | 6/2018 |

OTHER PUBLICATIONS

International Search Report and Written Opinion for Application No. PCT/US2020/025655, dated Jul. 22, 2020, 8 pages.
International Search Report and Written Opinion for Application No. PCT/US2019/019501, dated May 9, 2019, 8 pages.
International Search Report and Written Opinion for Application No. PCT/US2020/054568, dated Jan. 29, 2021, 13 pages.
International Preliminary Reporton Patentability for Application No. PCT/US2019/019501, dated Sep. 3, 2020, 7 pages.
International Search Report and Written Opinion for Application No. PCT/US19/17646, dated Apr. 16, 2019, 11 pages.
International Search Report and Written Opinion for Application No. PCT/US2019/056979, dated Dec. 18, 2019, 8 pages.
International Search Report and Written Opinion for Application No. PCT/US2019/062344, dated Mar. 23, 2020, 17 pages.
International Search Report and Written Opinion for Application No. PCT/US2019/062768, dated Mar. 9, 2020, 15 pages.
International Search Report and Written Opinion for Application No. PCT/US2019/064861, dated Mar. 30, 2020, 18 pages.
International Search Report and Written Opinion for Application No. PCT/US2019/066513, dated Apr. 21, 2020, 8 pages.
International Search Report and Written Opinion for Application No. PCT/US2019/066530, dated Apr. 21, 2020, 8 pages.
International Search Report and Written Opinion for Application No. PCT/US2020/020672, datd Jun. 29, 2020, 10 pages.
International Search Report and Written Opinion for Application No. PCT/US2020/033481, dated Sep. 3, 2020, 22 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Search Report and Written Opinion for Application No. PCT/US2021/012284, dated May 6, 2021, 23 pages.
European Search Report (Corrected version) for Application No. EP19750317.0, dated Mar. 28, 2022, 26 pages.
Partial European Search Report for Application No. EP19757451.0, dated Feb. 2, 2022, 12 pages.
Supplementary European Search Report for Application No. EP19873128.3, dated Jun. 22, 2022, 7 pages.

\* cited by examiner

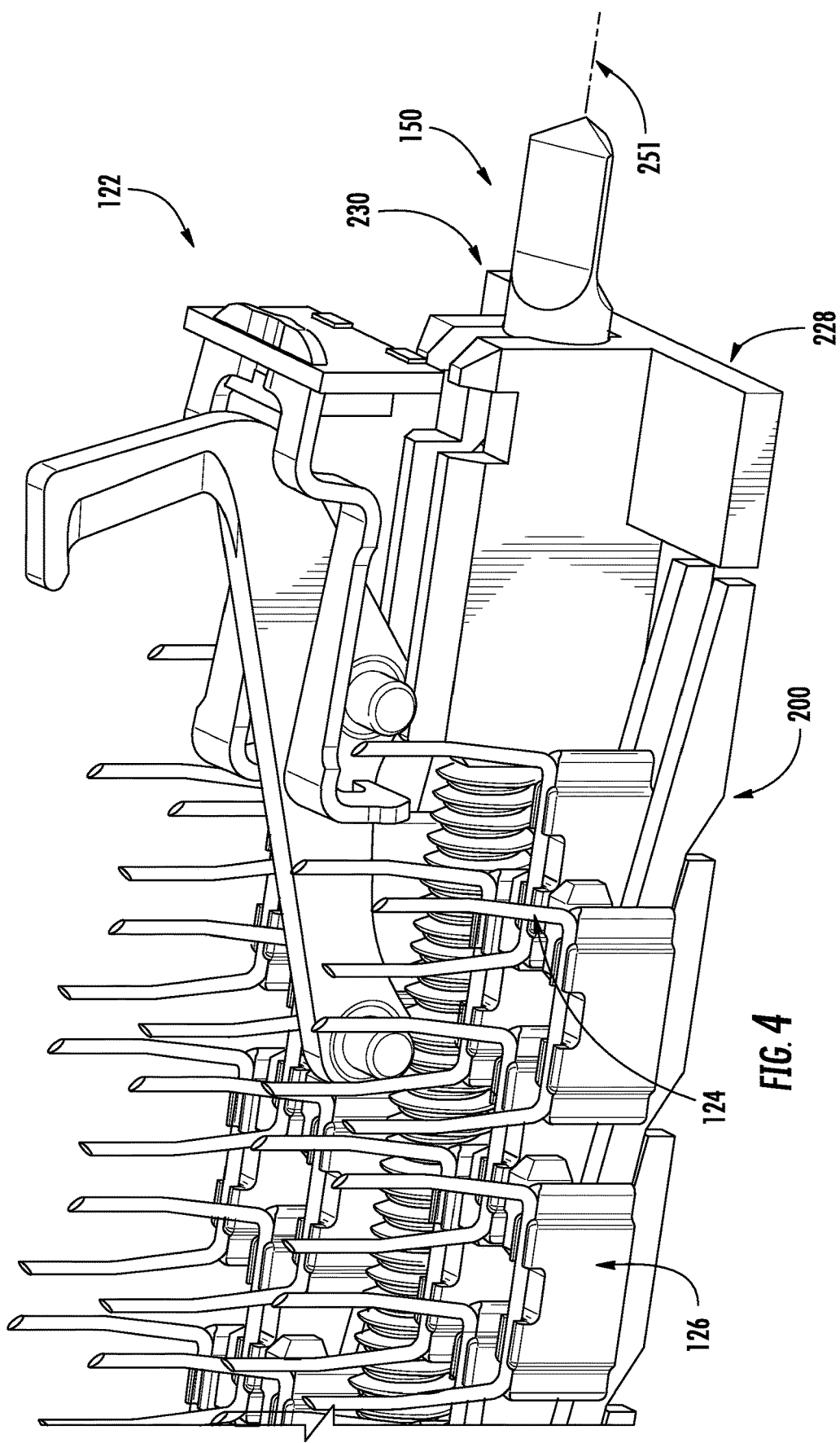

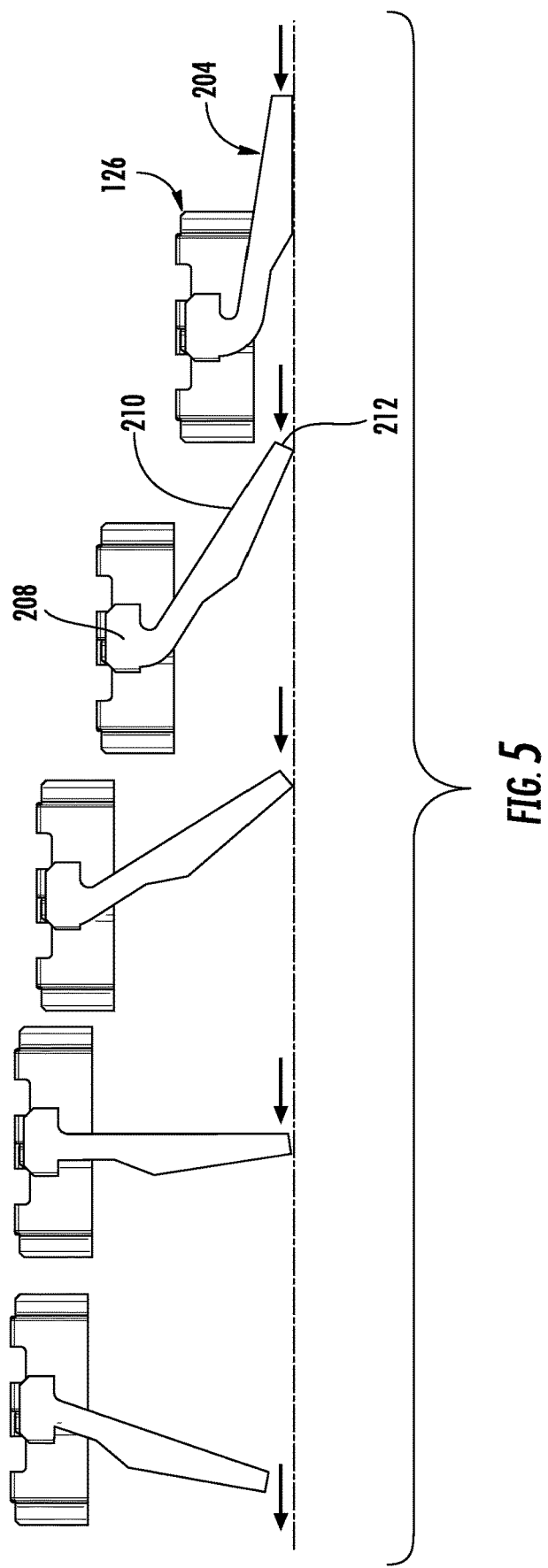

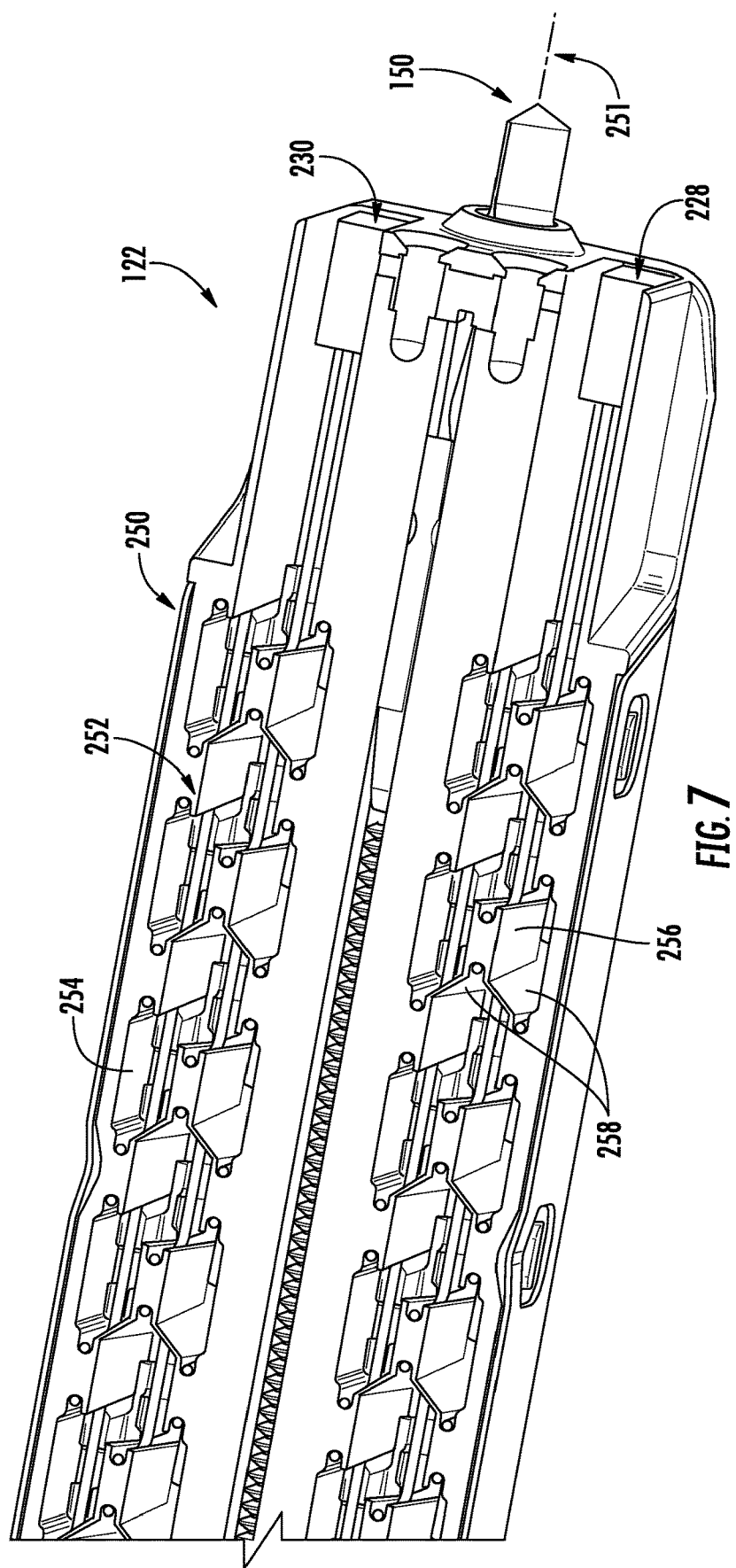

STAPLE CARTRIDGE AND DRIVE MEMBER FOR SURGICAL INSTRUMENT

CROSS-REFERENCE TO RELATED APPLICATIONS

This application claims the benefit of U.S. Provisional Application Ser. No. 62/961,504, filed Jan. 15, 2020, the entire disclosure of which is incorporated herein by reference for all purposes.

BACKGROUND

The field of the present disclosure relates to medical instruments, and more particularly to tissue sealing instruments for use in surgeries. Even more particularly, the present disclosure relates to a surgical stapling instrument having an improved staple cartridge and drive member (i.e., staple actuator) that allows for a smaller and more compact device.

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. The average hospital stay for a standard open surgery is typically significantly longer than the average stay for an analogous minimally invasive surgery (MIS). Thus, increased use of MIS could save millions of dollars in hospital costs each year. While many of the surgeries performed each year in the United States could potentially be performed in a minimally invasive manner, only a portion of the current surgeries uses these advantageous techniques due to limitations in minimally invasive surgical instruments and the additional surgical training involved in mastering them.

Improved surgical instruments such as tissue access, navigation, dissection and sealing instruments have enabled MIS to redefine the field of surgery. These instruments allow surgeries and diagnostic procedures to be performed with reduced trauma to the patient. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console, which in turn control motion of the servo-mechanically operated slave instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI™ system commercialized by Intuitive Surgical, Inc. of Sunnyvale, Calif.

A variety of structural arrangements have been used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. No. 7,594,912 (filed Sep. 30, 2004), 6,758,843 (filed Apr. 26, 2002), 6,246,200 (filed Aug. 3, 1999), and 5,800,423 (filed Jul. 20, 1995), the full disclosures of which are incorporated herein by reference in their entirety for all purposes. These linkages often manipulate an instrument holder to which an instrument having a shaft is mounted. Such a manipulator structure can include a parallelogram linkage portion that generates motion of the instrument holder that is limited to rotation about a pitch axis that intersects a remote center of manipulation located along the length of the instrument shaft. Such a manipulator structure can also include a yaw joint that generates motion of the instrument holder that is limited to rotation about a yaw axis that is perpendicular to the pitch axis and that also intersects the remote center of manipulation. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially hazardous forces against the abdominal wall. Alternative manipulator structures are described, for example, in U.S. Pat. No. 6,702,805 (filed Nov. 9, 2000), 6,676,669 (filed Jan. 16, 2002), 5,855, 583 (filed Nov. 22, 1996), 5,808,665 (filed Sep. 9, 1996), 5,445,166 (filed Apr. 6, 1994), and 5,184,601 (filed Aug. 5, 1991), the full disclosures of which are incorporated herein by reference in their entirety for all purposes.

During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices. Manipulation and control of these end effectors is a particularly beneficial aspect of robotic surgical systems. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastrointestinal tract. Many known surgical clamping and cutting devices, including known surgical staplers, have opposing jaws that clamp tissue and an articulated knife to cut the clamped tissue.

Surgical clamping and cutting instruments are often deployed into restrictive body cavities (e.g., through a cannula to inside the pelvis). Accordingly, it is desirable for the surgical clamping and cutting instrument to be both compact and maneuverable for best access to and visibility of the surgical site. Known surgical clamping and cutting instruments, however, may fail to be both compact and maneuverable. For example, known surgical staplers may lack maneuverability with respect to multiple degrees of freedom (e.g., Roll, Pitch, and Yaw) and associated desired ranges of motion.

Conventional surgical clamping and cutting instruments often include a staple cartridge designed to fit within the movable jaw of the end effector. The staple cartridge typically contains multiple rows of staple assemblies that each includes at least one staple and an associated staple driver or pusher. The staple pusher holds the staple in place prior to use. When the instrument is actuated, a drive member or staple actuator is configured to translate distally through the end effector and advance the staple pushers substantially perpendicular to the movable jaw, thereby driving the staples into the tissue.

The requisite size and shape of the drive member, however, limits the ability of the designer to reduce the size and shape of the overall surgical instrument. Typical drive members include a shuttle having one or more inclined distal surfaces or ramps configured to drive the staple pushers and their associated staples upwards into tissue as the drive member advances distally through the end effector. The ramps, however, must extend almost all the way to the top surface of the staple cartridge in order to drive the staples into the tissue when the instrument is actuated. To accommodate the ramps of the drive member, the staple cartridge typically includes a somewhat bulky nose extending from its distal end that prevents the ramps from contacting tissue when it reaches the most distal point of its translation through the end effector. The staple cartridge nose increases the length of the surgical instrument and may inhibit access to certain areas of the surgical site.

In addition, the staple cartridge typically includes extensive cutouts through its elongate body to provide sufficient clearance for the passage of the drive member ramps. These cutouts reduce the overall material strength of the staple cartridge and provide challenges and extra costs to the manufacturing process.

Accordingly, while the new telesurgical systems and devices have proven highly effective and advantageous, still further improvements would be desirable. In general, it would be desirable to provide improved surgical instruments that are more compact and maneuverable to enhance the efficiency and ease of use of minimally invasive systems. More specifically, it would be beneficial to create improved drive members and/or staple cartridges that will allow for the design of even more compact and maneuverable surgical instruments.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

In one aspect of the invention, a surgical instrument comprises a staple cartridge having a housing containing a staple pusher and a staple. The surgical instrument further includes a drive member or staple actuator configured to translate longitudinally through the instrument. The drive member includes a substantially elongate body and a projection extending laterally outward from the body. The lateral projection is configured to engage the staple pusher and drive the staple pusher in a direction transverse to the longitudinal axis of the staple cartridge housing. The lateral projection of the drive member has a height substantially less than the height of the staple cartridge housing, thereby requiring less clearance as it translates through the staple cartridge. In addition, the lateral projection has a smaller footprint than conventional drive members resulting in a more compact distal tip on the staple cartridge, which allows for a more compact and maneuverable surgical instrument.

In a preferred embodiment, the surgical instrument comprises an end effector with a first fixed jaw and a second jaw. The second jaw is configured to move relative to the first jaw from an open to a closed position. The staple cartridge is coupled to the second jaw and the drive member is configured to translate distally and retract proximally through the end effector. The drive member includes a projection or shuttle fin extending laterally outward to engage the staple pushers within the staple cartridge as the drive member is translated therethrough. The height of the shuttle fin is substantially smaller than the overall height of the drive member and the staple cartridge, preferably less than half the height of the staple cartridge and more preferably less than a fourth the height of the staple cartridge. This configuration minimizes the volume of space occupied by the shuttle fin when it is advanced to the distal tip of the staple cartridge, allowing for the design of a more compact nose. In addition, the relatively smaller shuttle fin reduces the volume of clearance space required for the drive member to translate through the staple cartridge, which allows the staple cartridge to be manufactured with more material and less cutouts than conventional designs, thereby increasing the material strength of the cartridge and decreasing the cost and complexity of the molding process.

In an exemplary embodiment, the staple cartridge comprises a drive rod pivotally coupled to the staple pusher. The drive rod includes a proximal end configured for receiving the shuttle fin of the drive member upon distal translation of the drive member through the staple cartridge. The engagement of the shuttle fin with the proximal end of the drive rod causes the drive rod to pivot about a hinge and drive the staple pusher in a perpendicular direction relative to the longitudinal axis of the staple cartridge. The drive rod may have an elongate portion extending proximally from the staple pusher. The elongate portion pivots from a substantially longitudinal orientation to a substantially perpendicular orientation relative to the staple cartridge. After it has been pivoted to the perpendicular orientation, the elongate portion of the drive rod has a length or height sufficient to advance the staple pusher close enough to the top surface of the staple cartridge such that the staples are driven into the patient's tissue.

In certain embodiments, the surgical instrument further includes an actuation mechanism in contact with the central portion of the drive member. The actuation mechanism is configured to advance the drive member distally through the end effector and to retract the drive member proximally through the end effector. In an exemplary embodiment, the actuator includes a control device of a robotic telesurgical system that may, for example, allow for mechanical actuation and control of the surgical instrument to perform a variety of functions, such as grasping a blood vessel, dissecting tissue, or the like, in response to manipulation of master input devices located remotely from the surgical instrument.

In another aspect, a surgical instrument comprises a staple cartridge having a housing containing a staple, a staple pusher and a drive rod pivotally coupled to the staple pusher. The instrument further includes a drive member configured to translate longitudinally through the housing and engage the drive rod to pivot the drive rod with respect to the staple pusher and thereby advance the staple pusher and associated staple in a direction transverse to the longitudinal axis of the housing. The drive rod is preferably sized and configured to pivot about the staple pusher and advance the staple a sufficient distance to drive the staple into tissue when the instrument is actuated.

In the preferred embodiment, the drive rod includes an elongate portion with a proximal end for receiving the drive member and a curved portion coupled to the staple support. Distal translation of the drive member engages the proximal end of the drive rod and advances it distally, causing the curved portion of the drive rod to deform and pivot about the staple pusher such that the staple pusher and staple are driven in a direction substantially perpendicular to the longitudinal axis of the staple cartridge. The elongate portion of the drive rod preferably extends in the longitudinal direction near the bottom surface of the staple cartridge housing prior to actuation. During actuation, the elongate portion has a length sufficient to advance the staple pusher substantially to the top surface of the staple cartridge. Thus, the pivotable drive rod and lateral projection of the present disclosure together perform substantially the same function as a ramp on a conventional drive member, thereby allowing for the design of a drive member without such a ramp.

In another aspect, a staple cartridge for a surgical instrument comprises a staple support, such as a staple driver or pusher, comprising an elongate body with a top surface configured for receiving a staple and a drive rod pivotally coupled to the staple support and configured to translate the staple support in a direction transverse to the elongate body. The staple cartridge may be configured for use with a surgical instrument having a drive member, such as described herein.

In certain embodiments, the cartridge further includes a hinge pivotally coupling the drive rod to the staple support. The hinge may be integral with the drive rod. The drive rod comprises an elongate portion coupled to a curved portion, which is coupled to the elongate body of the staple support. The elongate portion may have an end surface, wherein movement of the end surface in a first direction causes movement of the staple support in a second direction transverse to the first direction.

It is to be understood that both the foregoing general description and the following detailed description are exemplary and explanatory only and are not restrictive of the disclosure. Additional features of the disclosure will be set forth in part in the description which follows or may be learned by practice of the disclosure

BRIEF DESCRIPTION OF THE DRAWINGS

The above and other aspects, features, and advantages of the present surgical instruments will become more apparent in light of the following detailed description when taken in conjunction with the accompanying drawings in which:

FIG. 4 is a perspective side view of one portion of a staple cartridge with the drive member of FIG. 2B according to certain embodiments of the present invention;

FIG. 5 is a side view illustrating the actuation of the staple assembly of FIG. 2A;

FIG. 7 is a perspective top view of one portion of a staple cartridge according to certain embodiments of the present invention;

DETAILED DESCRIPTION

Figure 1:
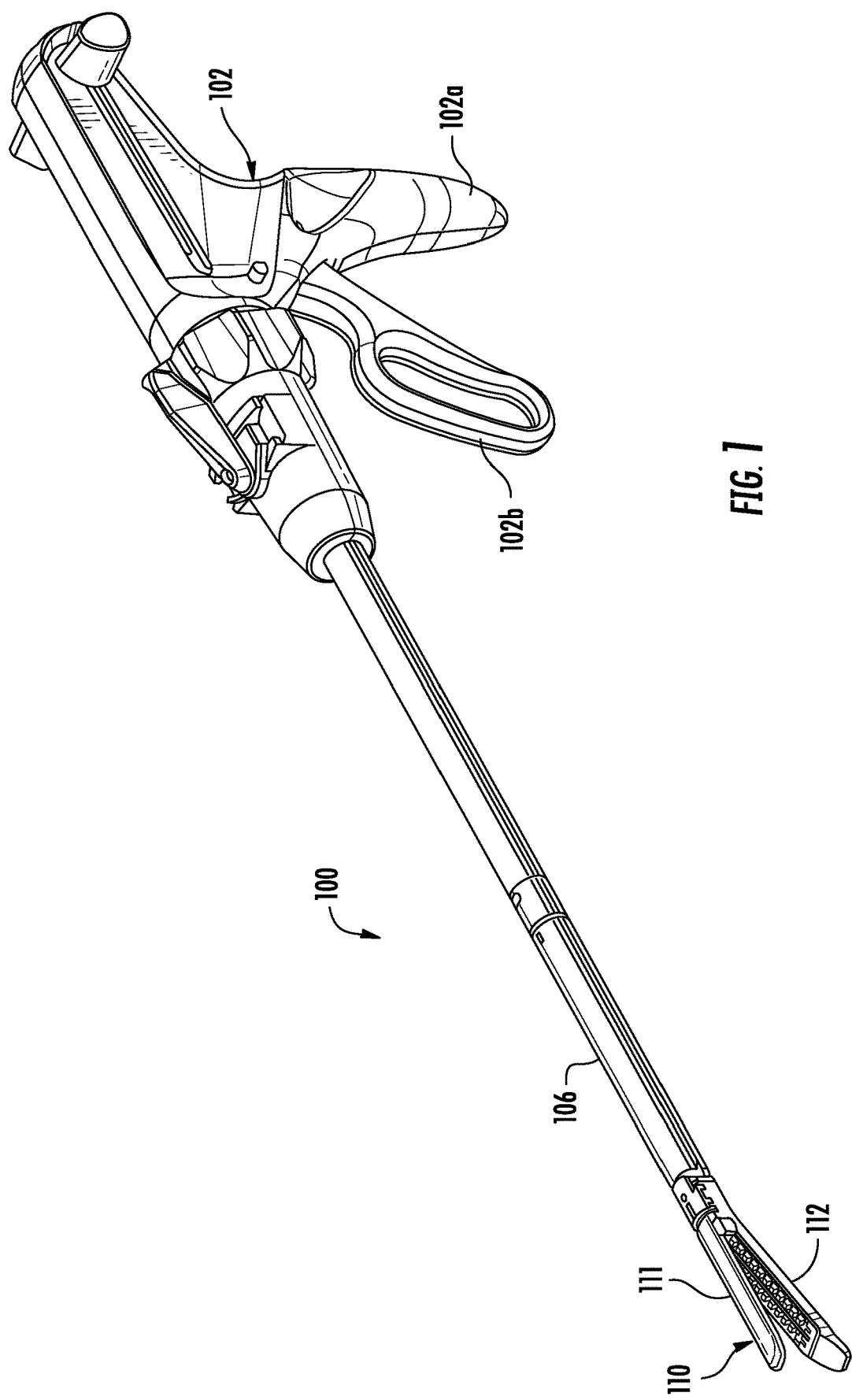
FIG. 1 is a perspective view of an illustrative surgical instrument having an end effector mounted to an elongated shaft, and an actuation mechanism.

Particular embodiments of the present surgical instruments are described hereinbelow with reference to the accompanying drawings; however, it is to be understood that the disclosed embodiments are merely exemplary of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in any unnecessary detail. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or illustrated components.

While the following disclosure is presented with respect to a linear surgical stapler where staples are sequentially fired, it should be understood that the features of the presently described surgical instruments may be readily adapted for use in any type of surgical clamping, cutting, ligating, dissecting, clipping, cauterizing, suturing and/or sealing instrument, whether or not the surgical instrument applies a fastener. For example, the presently described drive member and actuation mechanism may be employed in an electrosurgical instrument wherein the jaws include electrodes for applying energy to tissue to treat (e.g., cauterize, ablate, fuse, or cut) the tissue. The surgical clamping and cutting instrument may be a minimally invasive (e.g., laparoscopic) instrument or an instrument used for open surgery.

The embodiments of the present disclosure may also be incorporated into the a variety of different surgical instruments, such as those described in commonly-assigned, co-pending U.S. patent application Ser. Nos. 16/205,128, 16/427,427, 16/678,405, 16/904,482, 17/081,088 and 17/084,981 and International Patent Nos. PCT/US2019/107646, PCT/US2019/019501, PCT/US2019/062344, PCT/US2020/54568, PCT/US2019/064861, PCT/US2019/062768, PCT/2020/025655, PCT/US2020/056979, PCT/2019/066513, PCT/US2020/020672, PCT/US2019/066530 and PCT/US2020/033481, the complete disclosures of which are incorporated by reference herein in their entirety for all purposes as if copied and pasted herein.

Additionally, the features of the presently described surgical stapling instruments may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

FIG. 1 is a perspective view of an illustrative surgical stapling instrument 100 in accordance with certain embodiments of the present disclosure having a handle assembly 102, and an end effector 110 mounted on an elongated shaft 106 of the surgical stapling instrument 100. End effector 110 includes a stationary jaw 111 and a moveable jaw 112. Handle assembly 102 includes a stationary handle 102a and a moveable handle 102b, which serves as an actuator for surgical instrument 100.

In certain embodiments, handle assembly 102 may include input couplers (not shown) instead of, or in addition to, the stationary and movable handles. The input couplers provide a mechanical coupling between the drive tendons or cables of the instrument and motorized axes of the mechanical interface of a drive system. The input couplers may interface with, and be driven by, corresponding output couplers (not shown) of a telesurgical surgery system, such as the system disclosed in U.S. Pub. No. 2014/0183244A1, the entire disclosure of which is incorporated by reference herein. The input couplers are drivingly coupled with one or more input members (not shown) that are disposed within the instrument shaft 106 and end effector 110. Suitable input couplers can be adapted to mate with various types of motor packs (not shown), such as the stapler-specific motor packs disclosed in U.S. Pat. No. 8,912,746, or the universal motor packs disclosed in U.S. Pat. No. 8,529,582, the disclosures of both of which are incorporated by reference herein in their entirety. Further details of known input couplers and surgical systems are described, for example, in U.S. Pat. Nos. 8,597,280, 7,048,745, and 10,016,244. Each of these patents is hereby incorporated by reference in its entirety.

Actuation mechanisms of surgical instrument 100 may employ drive cables that are used in conjunction with a system of motors and pulleys. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated by reference in their entireties. While described herein with respect to an instrument configured for use with a robotic surgical system, it should be understood that the wrist assemblies described herein may be incorporated into manually actuated instruments, electro-mechanical powered instruments, or instruments actuated in any other way.

Figure 1A:
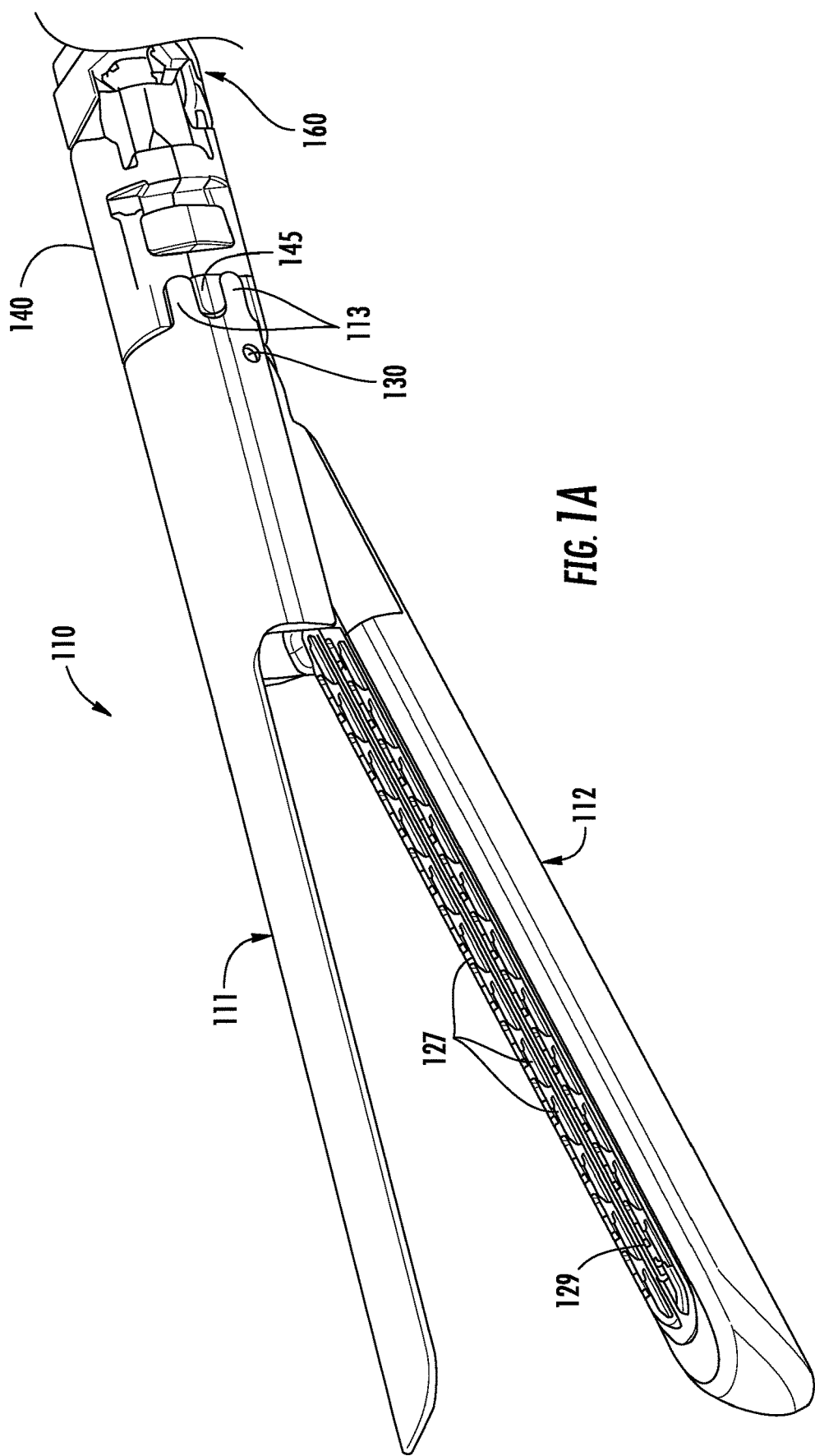
FIG. 1A is a perspective top view of the distal end portion of an illustrative surgical instrument with the jaws in the open position.

FIG. 1A illustrates the distal end portion of surgical instrument 100, including an end effector 110 having a first jaw 111 and a second jaw 112, a clevis 140 for mounting jaws 111, 112 to the instrument, and an articulation mechanism, such as a wrist 160. In certain embodiments, second jaw 112 is a movable jaw configured to move from an open position to a closed position relative to first jaw 111. In other embodiments, first jaw 111 is a movable jaw configured to move between open and closed positions relative to second jaw 112. In still other embodiments, both jaws 111, 112 are movable relative to each other. First jaw 111 may include an anvil 115 having staple-forming pockets 116 (see FIG. 1D). In the open position, a fresh stapling cartridge 122 (sometimes referred to as a reload and shown more clearly in FIG. 1B) can be loaded into movable jaw 112 and tissue may be positioned between the jaws 111, 112. In the closed position, jaws 111, 112 cooperate to clamp tissue such that cartridge 122 and the anvil 115 are in close cooperative alignment.

Figure 1B:
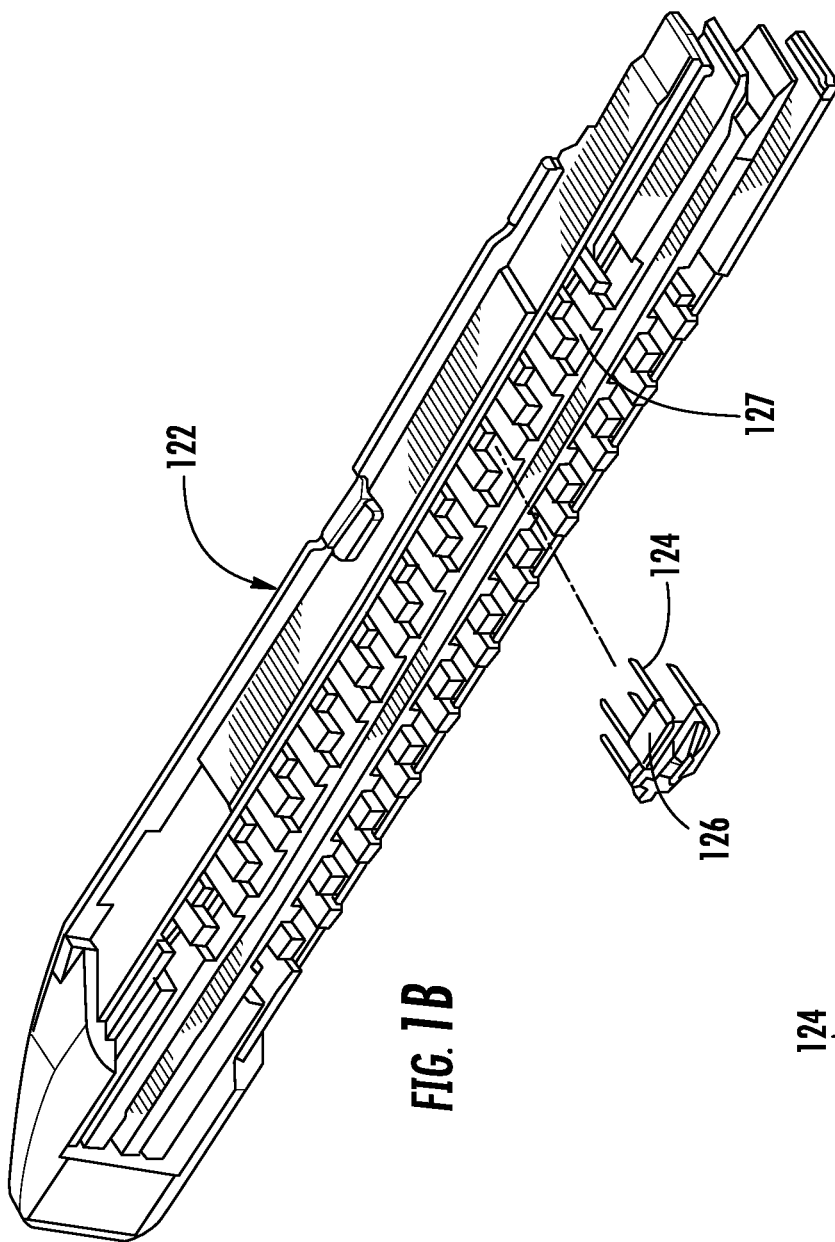
FIG. 1B is a bottom perspective view with parts separated of a representative staple cartridge for an illustrative surgical instrument.
Figure 1C:
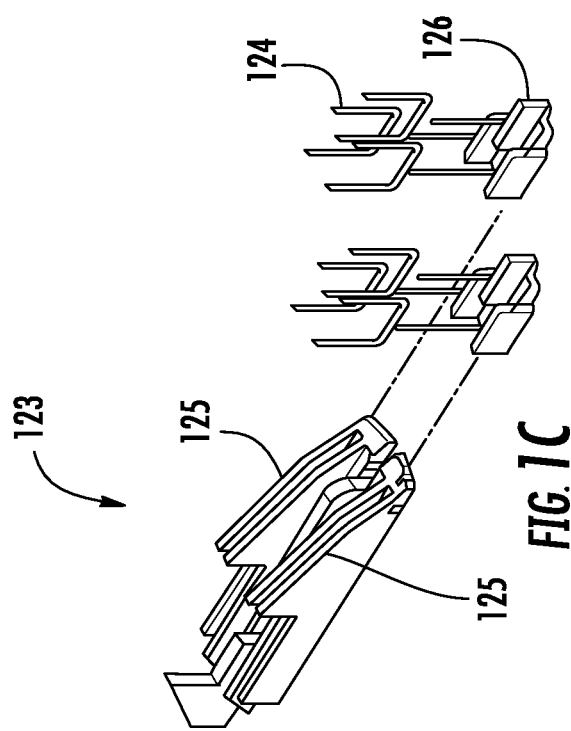
FIG. 1C shows an enlarged view of the cooperative relationship between a plurality of conventional staple pushers and staples which form part of the staple cartridge of FIG. 1B.
Figure 1D:
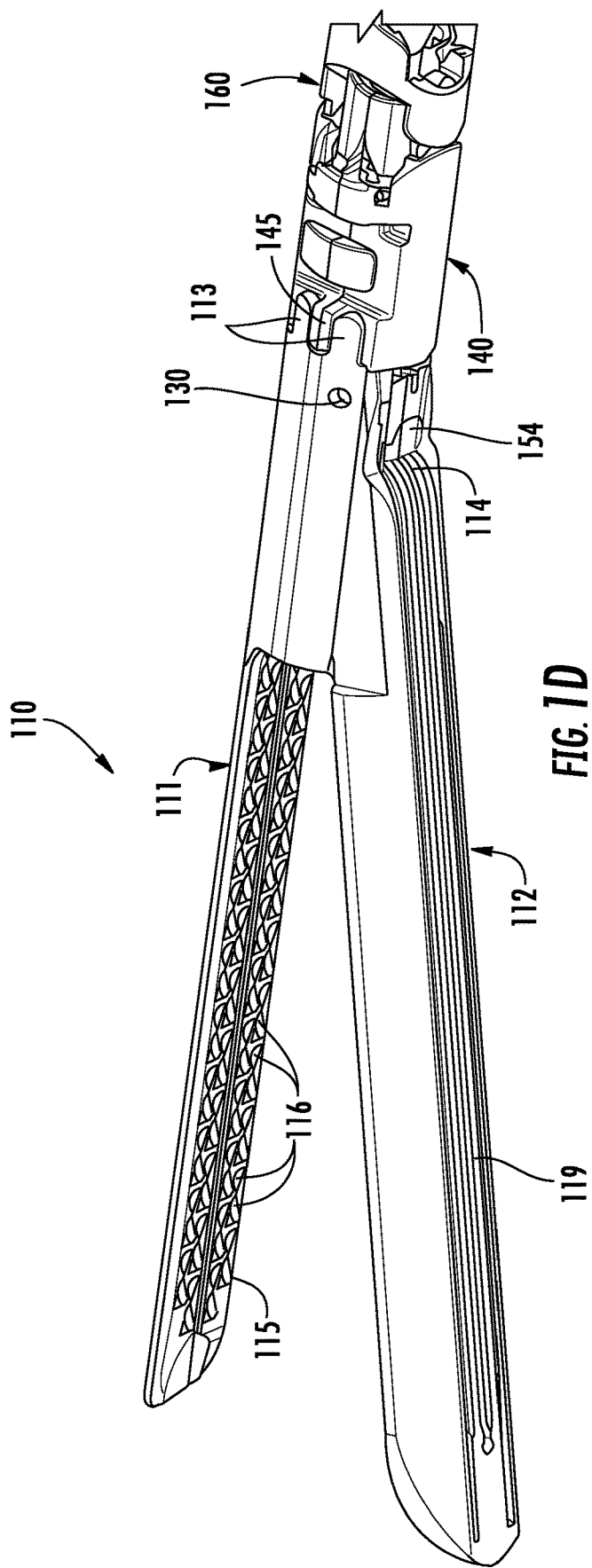
FIG. 1D is a perspective bottom view of the distal end portion of the surgical instrument of FIG. 1A.

Referring now to FIGS. 1B and 1C, a representative cartridge 122 is shown to illustrate the basic features of a conventional surgical staple instrument. Cartridge 122 may include a plurality of staples 124 supported on corresponding staple pushers 126 provided within respective staple apertures 127 formed in cartridge 122. A drive member 150 (shown in FIG. 2B), may be translated distally through end effector 110 to sequentially act on staple pushers 126, driving them upwardly, thereby moving staples 124 into deforming contact with anvil 115 (discussed in more detail below). Cartridge 122 may be removably received within movable jaw 112 or, in single use embodiments, may be manufactured as part of movable jaw 112.

Figure 2A:
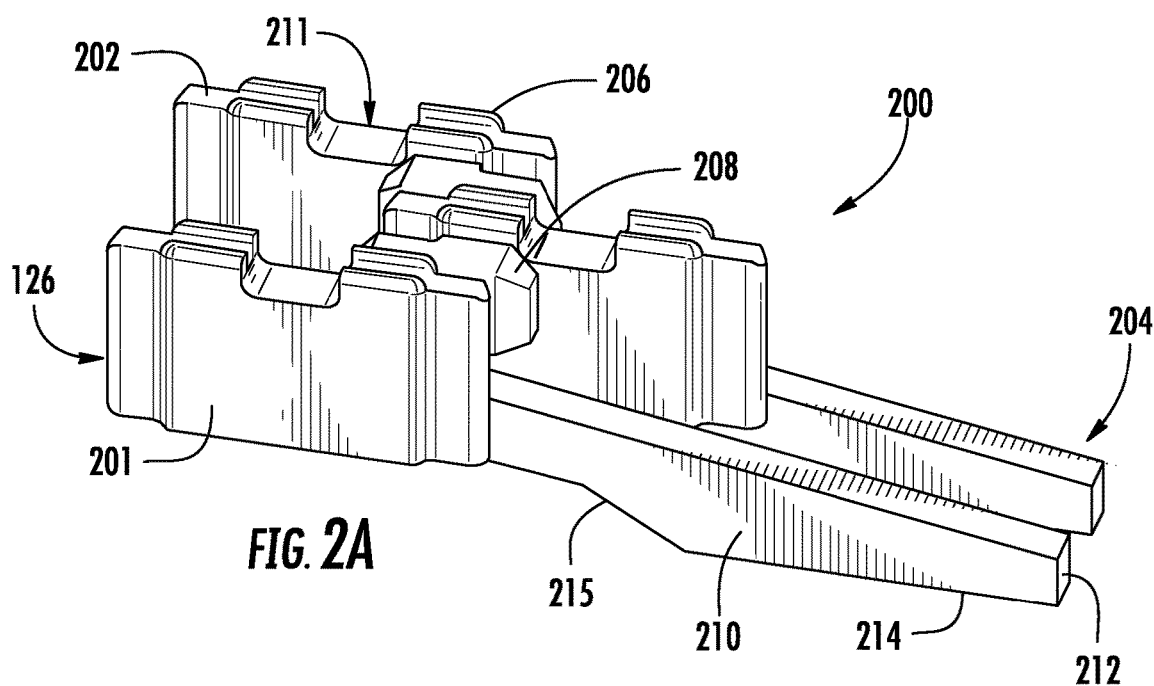
FIG. 2A is a perspective side view of a staple assembly according to certain embodiments of the present disclosure.
Figure 3:
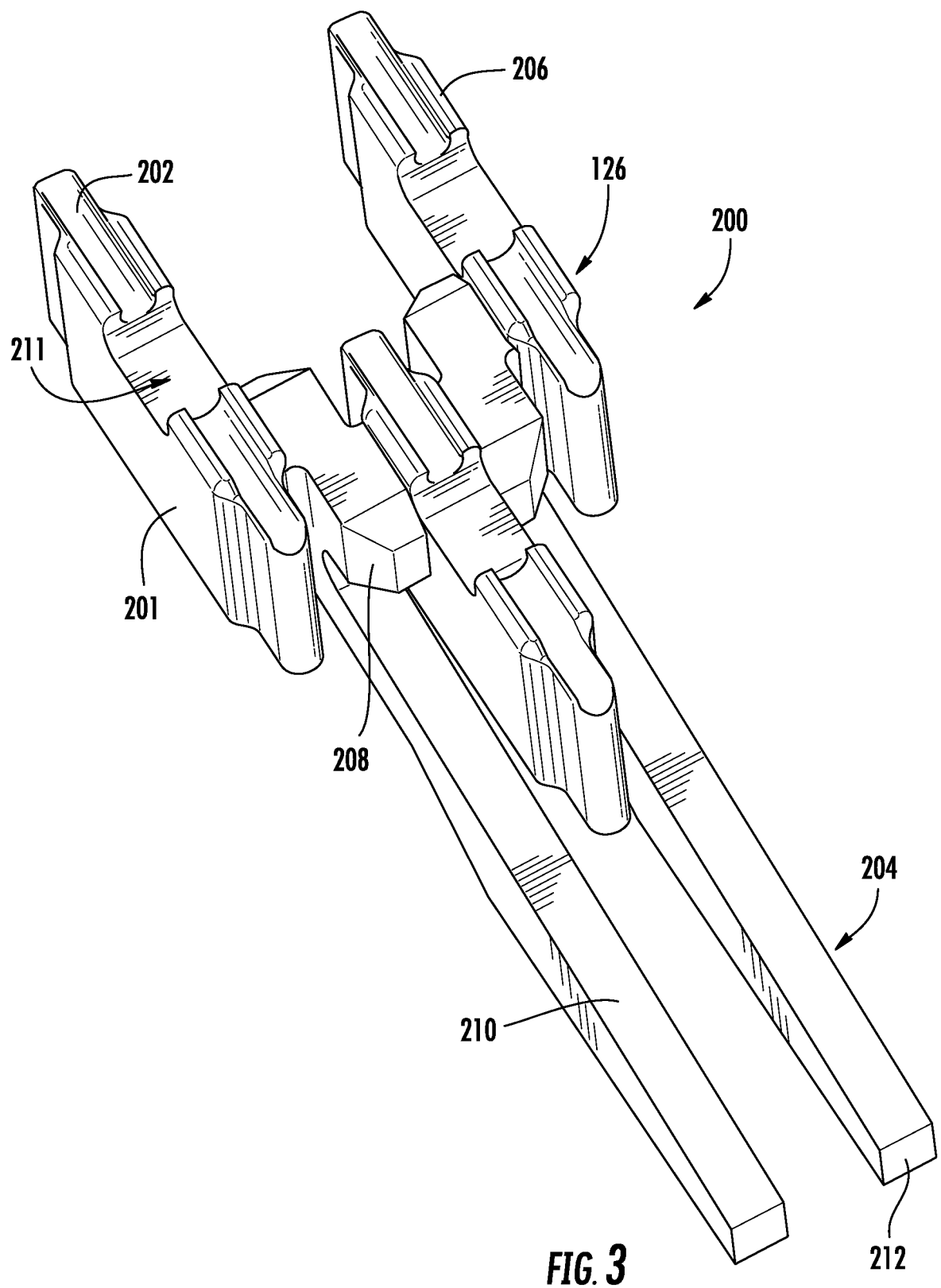
FIG. 3 is a perspective top view of the staple assembly of FIG. 2A.

FIGS. 2A and 3 illustrate a preferred embodiment of a staple assembly 200 according to the present invention. As shown, staple assembly 200 includes one or more staple pushers 126 (preferably about 2 to 4) each having a substantially elongate body 201 with a top surface 202 configured for receiving one or more staples 124 (not shown in FIG. 2A). In an exemplary embodiment, staple pusher(s) 126 include one or more supporting elements 206 extending above top surface 202 for providing support to staples 124 when they are resting on top surface 202. Of course, other suitable geometric designs of staple pusher 126 may be used to receive and hold staple 124 in accordance with the present invention. For example, pusher 126 may have a longitudinal recess (not shown) for receiving staple 124, as is described in commonly-assigned, co-pending International Patent Application No. PCT/US2020/033481, filed May 18, 2020, the complete disclosure of which is incorporated herein by reference for all purposes. Alternatively, staple pusher 126 may have a flatter upper surface (i.e., without a recess or pocket) that allows the backspan of staple 124 to rest thereon, as is described in commonly-assigned, provisional patent application No. 62/783,460. The complete disclosure of both applications are hereby incorporated by reference in their entirety for all purposes.

Staple assembly 200 further comprises one or more drive rods 204 coupled to staple pusher(s) 126. Drive rods 204 each comprise a curved portion 208 preferably coupled to the side surface of staple pusher body 201 and an elongate portion 210 extending in a substantially longitudinal direction away from staple pusher 202. Elongate portions 210 each include a proximal end 212 for engagement with drive member 150 (discussed below) and a bottom surface 214 configured to reside on, or near, the bottom inside surface of suture cartridge 122. In an exemplary embodiment, elongate portion 210 of drive rod 204 further includes an inclined surface or ramp 215 between bottom surface 214 and curved portion 208. Ramp 215 serves to elevate staple pusher body 201 above the proximal part of elongate portion 210 to provide room for adjacent staple pushers 126 in cartridge 122 (see FIG. 4 wherein each staple pusher body 201 resides above the proximal portion of the drive rod 204 for the adjacent staple pusher 126). Ramp 215 may also provide additional leverage to enable elongate portion 210 to pivot about staple pusher 126, as discussed in more detail below.

Referring now to FIG. 5, curved portions 208 function as a living hinge or flexure bearing between drive rods 204 and staple pushers 126. To that end, curved portions 208 preferably have a shape and size specifically designed to allow drive rod 204 to pivot or rotate with respect to staple pusher 126. Curved portions 208 may include a thinned material portion (not shown) that deforms as drive rod 204 is pivoted about pusher body 201 to facilitate the formation of the living hinge. Curved portions 208 (and the entire drive rod 204) may be formed integrally with staple pusher 126, or they may be formed separately and then suitably coupled thereto. As shown, a sufficient force applied to proximal end 212 of drive rod 204 causes drive rod 204 to pivot about the hinge formed by curved portion 208, thereby driving staple pusher 126 in a substantially perpendicular direction to the applied force. In particular, curved portion 208 deforms from the curved orientation shown in the leftmost picture to a substantially straight orientation as shown in the rightmost picture. This deformation allows elongate portion 210 to rotate from the longitudinal orientation to the perpendicular orientation, thereby driving staple pusher 126 vertically relatively to staple cartridge 122. Of course, other suitable hinges may be used with the present disclosure, such as a pin, bolt, joint hinge, strap hinge, butterfly, barrel, piano, pivot, spring and the like.

Staple pusher 126 preferably includes a groove or other recess 211 in top surface 202 for receiving a projection (not shown) in staple cartridge 122. Recess 211 is sized to engage with the cartridge projection and allow for movement of staple pusher 126 in a substantially perpendicular direction to the longitudinal axis of the cartridge housing. The cartridge projection preferably cooperates with a vertical rail member to restrict movement of projection and staple pusher 126 to a substantially vertical path. Recess 211 and the cartridge projection ensure that when drive member 150 is translated distally and engages with proximal end 212 of drive rods 204, that staple pusher 126 and staple 124 do not also move distally and are instead driven upwards relative to cartridge 122 so that staple 124 is ultimately driven into the tissue when movable jaw 112 engages fixed jaw 110. In other embodiments, pusher 126 may be formed with a groove or recess in the side surface of body 201. For example, pusher 124 may have a projection or recess that cooperates with an associated vertical groove or recess in the staple cartridge. In alternative embodiments, other mechanisms can be used to ensure that staple pusher 124 is driven upwards into fixed jaw 110 during actuation. For example, cartridge 122 may include rails or other material at the distal end of each pusher 126 or staple assembly to prevent distal movement of staple assemblies when drive member 150 engages drive rods 204.

Elongate portion 210 of drive rod(s) 204 preferably has a length sufficient to drive staple pusher 126 close to, at, or even above, the top surface of staple cartridge 122. Thus, as drive member 150 moves proximal end 212 of drive rods 204 to a point where drive rods 204 are substantially perpendicular to their original orientation prior to actuation, staple pusher 126 has been advanced or lifted through staple cartridge 122 to the point where staple 124 can be driven into the patient's tissue. The exact length of elongate portion 210 will, of course, depend on the height of staple cartridge 122, and/or the height of staples 124, which may vary depending on the surgical application.

Of course, it will be recognized that the present disclosure is not limited to a drive rod pivotally coupled to staple pusher body 201. Other suitable actuating mechanisms can be used with the drive member 150 of the invention to move staple pusher 126 and staple 124 a sufficient distance to drive staple 124 into the patient's tissue. For example, staple cartridge 122 may comprises another actuator, such as a rotational actuator, linear actuator, or a biasing mechanism, such as a spring-loaded actuator, that receives drive member 150 and advances staple pusher 126 vertically relative to the cartridge housing 250. In the latter embodiment, the spring-loaded actuator will be configured to receive projections 228, 230 of drive member 150 and exert a spring force on pusher 126 to advance pusher 126 upwards relative to cartridge housing 250.

As shown in FIG. 4, staple cartridge 122 preferably includes multiple staple assemblies 200 spaced from each other in the longitudinal direction. Thus as shown in the leftmost portion of FIG. 5, curved portion 208 will preferably have sufficient flexibility to allow elongate portion 210 to be moved beyond, or distal to, a substantially perpendicular orientation such that proximal end 212 of elongate portion 210 is moved vertically upwards a sufficient distance to provide clearance for drive member 150 to pass distally of each staple pusher 126 and engage the next staple assembly 200 in staple cartridge 122.

Referring again to FIG. 3, in an exemplary embodiment, staple assembly 200 includes three staple pushers 126 and two drive rods 204 situated such that rods 204 are each coupled to two of the staple pushers 126. In particular, curved portions 208 of drive rods 204 are each coupled to one of the outer staple pushers 126 and a central staple pusher 126. Other suitable configurations may be utilized with the present invention. For example, drive rods 204 may be situated on the outside of stable assembly 200 such that they are each coupled to one of the outer staple pushers 126. Alternatively, staple assembly 200 may comprise three drive rods 204 each coupled to only one staple pusher 126. In yet another embodiment, staple assembly 200 includes only two staple pushers 126 with one drive rod 204 therebetween. Other suitable arrangements will be envisioned by those skilled in the art.

Referring now to FIGS. 4 and 7, a preferred embodiment of cartridge 122 will now be described. As shown, cartridge 122 includes an elongate housing 250 extending substantially along a longitudinal axis 251 and including a plurality of apertures or compartments 252 that form pockets 254 within the housing to receive staple assemblies 200. As mentioned previously, staple assemblies 200 each include at least one (preferably 2-4) staple pushers 126 removably coupled to at least one (preferably 2-4) staples 124. Staple assemblies 200 are preferably arranged within compartments 252 such that each staple pusher 126 is situated near a bottom surface of housing 250 and staples 124 have their legs facing a top surface of housing 250. For ease of reference, the top surface of housing faces fixed jaw 111 (see FIG. 1). As discussed above, the entire staple cartridge 122 can be loaded into movable jaw 112 for use in surgery as described in more detail below.

Figure 2B:
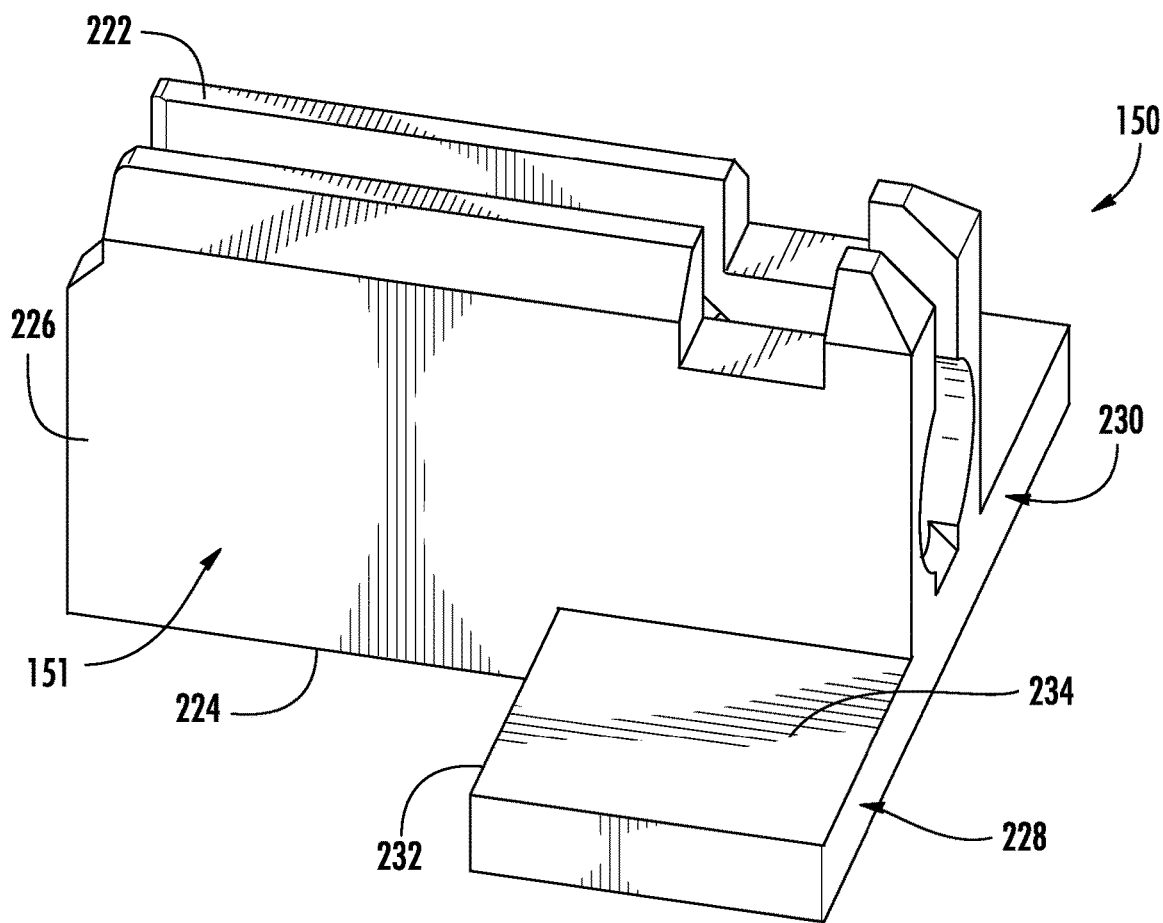
FIG. 2B is a perspective side view of a drive member according to certain embodiments of the present disclosure.

As shown in FIG. 2B, a preferred embodiment of drive member 150 includes a body 151 having a top surface 222, a bottom surface 224 and a pair of side surfaces 226 connecting top and bottom surfaces 222, 224. Drive member 150 further includes a pair of projections or shuttle fins 228, 230 extending laterally outward from side surfaces 226. Shuttle fins 228, 230 preferably comprise substantially flattened appendages extending from either side of drive member 150. Shuttle fins 228, 230 each include a distal end 232 configured to engage proximal ends 212 of drive rods 204 to drive pushers 126 (and the associated staples 124) vertically or perpendicular to the longitudinal axis when drive member 150 is translated in the distal direction. Distal ends 232 are preferably substantially perpendicular to the longitudinal axis of drive member 150, although it will be recognized that ends 232 may define an incline, ramp, recess, pocket or other design and still fulfill the purpose of engaging proximal ends 212 of drive rods 204. Shuttle fins 228, 230 are shown extending from the proximal portion of drive member body 151 with distal end 232 of each fin 228, 230 extending out from side surfaces 226. However, it should be noted that shuttle fins 228, 230 may reside closer to the distal portion of drive member 150 than shown in FIG. 2B so as to reduce the distance drive member 150 extends distally out from cartridge 122 after it has been moved to the final distal position (i.e., sufficiently far to engage all of the staple pushers 126 within cartridge 122).

Shuttle fins 228, 230 preferably extend laterally outward from body 151 a suitable distance to engage drive rods 204 (as best shown in FIG. 4). Shuttle fins 228, 230 preferably have a substantially planar top surface 234 that is preferably located below top surface 222 of drive member body 151. In the exemplary embodiment, shuttle fins 228, 230 have a height (as measured perpendicular to longitudinal axis 251) that is substantially less than the height of body 151. In an exemplary embodiment, the height of shuttle fins 228, 230 are less than half of the height of body 151, more preferably less than 25% of the height of body 151. Fins 228, 230 preferably extend from the bottom portion of drive member body 151 to minimize the vertical footprint of fins 228, 230.

Figure 6A:
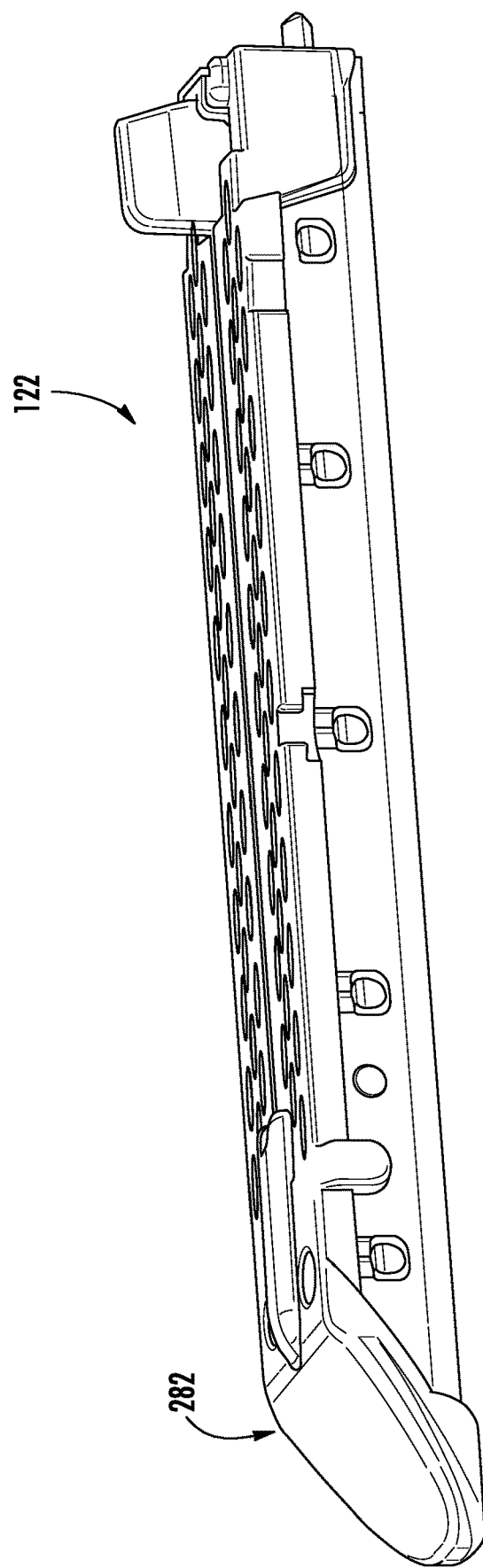
FIGS. 6A and 6B illustrate a conventional staple cartridge.

In conventional drive members (see FIGS. 6A and 6B), the shuttle fins have an inclined distal surface or ramp 280 that extends almost all the way to the top surface of staple cartridge housing 250. This ramp 280 is configured to engage the staple pushers and cam them upwards sufficiently far enough to drive the staples into tissue. To accommodate these shuttle fin ramps 280, staple cartridge 122 typically includes a somewhat bulk nose 282 extending from its distal end that prevents ramps 280 of the drive member from contacting tissue when it reaches the most distal point of its translation through the end effector. The staple cartridge nose 282 increases the length of the surgical instrument and may inhibit access to certain areas of the surgical site.

Figure 6B:
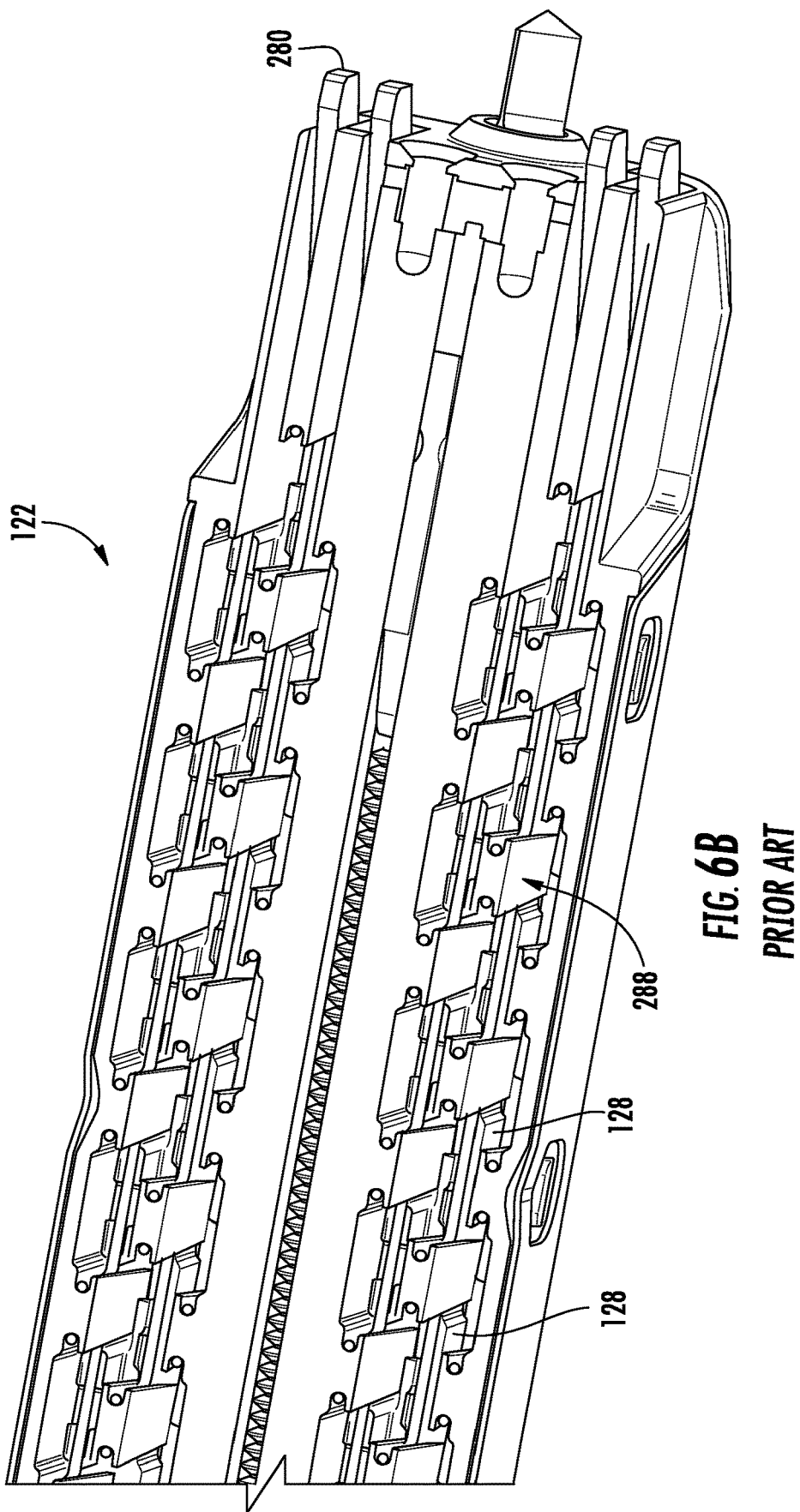

In addition, staple cartridge 122 typically includes extensive cutouts through its elongate body to provide sufficient clearance for the passage of the drive member ramps. FIG. 6B illustrates a conventional staple cartridge with a plurality of compartments for housing the staple pushers (not shown). As illustrated in FIG. 6B, the cartridge includes central support posts 288 completely surrounded by the cutouts to provide clearance for ramps 280. These cutouts reduce the overall material strength of the staple cartridge; and they provide challenges and extra costs to the manufacturing process.

By contrast, shuttle fins 228, 230 of the present disclosure have a much smaller footprint than conventional "ramp shuttle fins". As mentioned previously, they preferably extend to less than 50%, more preferably less than 25% of the height of the drive member 150, which allows the designer to provide more material in staple cartridge 122 (i.e., less cutouts). In addition, the more compact shuttle fins 228, 230 of the present disclosure allow for a shorter and more compact nose at the distal end of shuttle cartridge, which reduces the overall size of surgical instrument 100. In addition, having a more compact distal nose may allow the surgeon to access areas of the surgical site that would have been more difficult, or even impossible, with a larger and bulkier instrument.

FIG. 7 shows a portion of staple cartridge 122 that illustrates one of the advantages of the present invention. As shown, staple cartridge 122 generally includes an elongate housing 250 having a plurality of compartments 252 for housing staple assemblies 200. As mentioned previously, the preferred embodiment of each staple assembly 200 includes three staple pushers (not shown) with one central staple pusher positioned just proximal to two lateral pushers. Accordingly, housing 250 includes pockets 254 for each of the staple pushers with a central support post 256 situated near each staple assembly (central support post 256 generally being located behind the central staple pusher and between the two lateral staple pusher within each staple assembly 200). In contrast to conventional designs, however, an exemplary cartridge 122 further includes a pair of diagonal support walls 258 coupling each central support post 256 with the rest of staple cartridge. Although not shown in FIG. 7, these diagonal support walls 258 do not extend all the way to the bottom surface of staple cartridge 122. Instead, support walls 258 stop short of the bottom surface to provide clearance for shuttle fins 228, 230.

Diagonal support walls 258 provide additional strength to staple cartridge 122. In addition, the overall staple cartridge is less expensive and easier to mold because it does not require the extensive cutouts typically used in conventional devices.

Referring again to FIG. 2B, shuttle fins 228, 230 are preferably integrated into the lower portion of drive member 150 such that the bottom surface of fins 228, 230 reside at approximately the same level as bottom surface 224 of drive member body 151. This reduces the overall height and footprint take up by fins 228, 230. In addition, integrating shuttle fins 228, 230 into drive member 150 provides more flexibility in the design of surgical instrument 100. For example, this may allow for a reduction in the size of staple cartridge 122 and surgical instrument 100 and/or an increase in the length of staples 124 for a given size of surgical instrument 100.

Figure 8:
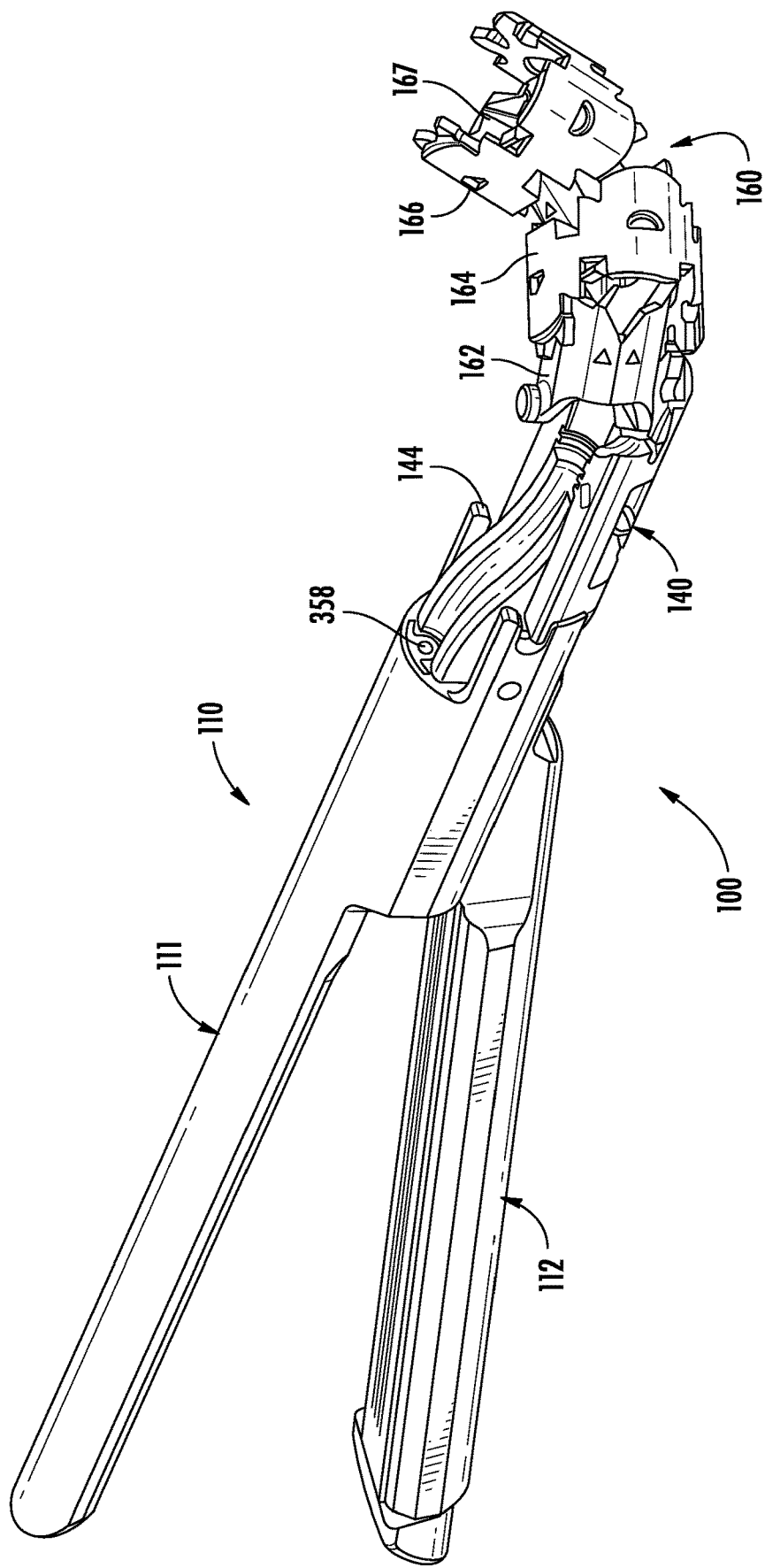
FIG. 8 is a perspective view of the end portion of an illustrative surgical instrument with parts removed.

Referring now to FIG. 8, in certain embodiments, jaws 111, 112 are attached to surgical instrument 100 via a clevis 140. Clevis 140 includes upper and lower portions that cooperate when assembled to form a protrusion 145 configured to engage tabs 113 (see FIG. 1A) of jaw 111 to securely mount jaw 111 in a fixed position on instrument 100. Clevis 140 further includes an opening for receiving a pivot pin 130 defining a pivot axis around which jaw 112 pivots as described in more detail below. A more complete description of a suitable clevis 140 for use with the present invention may be found in commonly-assigned, provisional patent application Nos. 62/783,444, filed Dec. 21, 2018; 62/783,481, filed Dec. 21, 2018; 62/783,460, filed Dec. 21, 2018; 62/747,912, filed Oct. 19, 2018; and 62/783,429, filed Dec. 21, 2018, the complete disclosures of which are hereby incorporated by reference in their entirety for all purposes. Of course, it will be recognized by those skilled in the art that other coupling mechanisms known by those skilled in the art may be used with the present invention to attach the jaws 11, 112 to the proximal portion of surgical instrument 100.

End effector 110 may be articulated in multiple directions by an articulation mechanism. In certain embodiments, the articulation mechanism may be a wrist 160 as shown, although other articulation mechanisms are contemplated. As seen in FIG. 8, a preferred embodiment of wrist 160 includes a plurality of articulation joints 162, 164, 166, etc. that define a bore 167 through which an actuation mechanism (in embodiments, coil 120 and drive cable 171, see FIGS. 9A and 9B) may pass. Upon exiting articulation wrist 160, coil 120 enters and passes through an internal channel (not shown) of clevis 140, ultimately engaging proximal surface 153 of upper shoe 152 of drive member 150. Other articulation mechanisms known by those skilled in the art may substitute for wrist 160. Other exemplary articulating mechanisms are shown for example in U.S. Publication. No. 2015/0250530 the entire disclosure of which is hereby incorporated by reference in its entirety for all purposes.

Figure 9A:
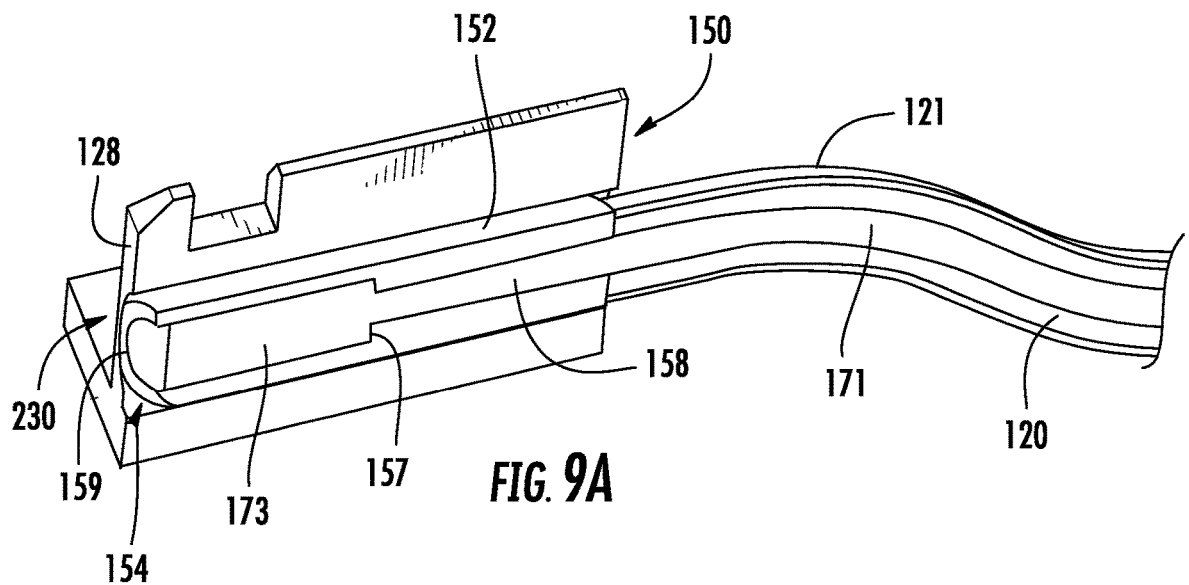
FIG. 9A is a partial cross-sectional perspective view of the actuation mechanism for a drive member in accordance with the surgical instrument of FIG. 1.
Figure 9B:
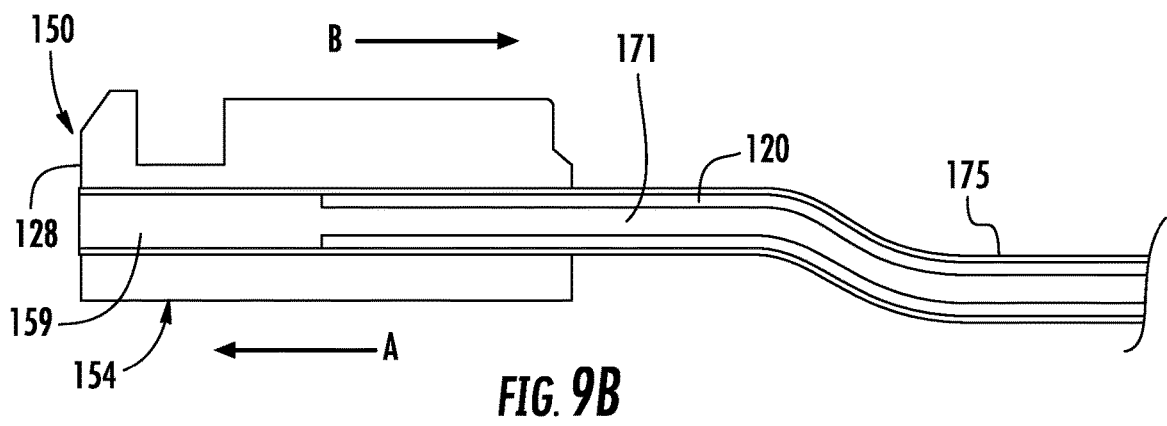
FIG. 9B is a partial cross-sectional side view of the actuation mechanism for a drive member in accordance with the surgical instrument of FIG. 1.

As seen in FIGS. 9A and 9B, an illustrative actuation assembly includes a drive cable 171, a coil 120, a sheath 121 surrounding coil 120, and a drive rod 175. Drive cable 171 includes an enlarged distal end 173. Upper shoe 152 of drive member 150 includes a bore 158 (see also FIG. 10) into which drive cables 171 are routed. When assembling illustrative surgical instrument 100, coil 120 and a protective sheath 121 are slipped over the free end of drive cable 171. The free end of drive cable 171 is attached to a drive rod 175 securing coil 120 and the protective sheath 121 between drive member 150 and drive rod 175. Sheath 121 may function to promote stability, smooth movement, and prevent buckling upon actuation of surgical instrument 100. Sheath 121 may be made from polyimide, or any other suitable material having the requisite strength requirements such as various reinforced plastics, a nickel titanium alloy such as NITINOL™, poly para-phenyleneterphtalamide materials such as KEVLAR™ commercially available from DuPont. Those of skill in the art may envision other suitable materials.

Enlarged distal end 173 of drive cable 171 resides within an enlarged distal portion 159 of bore 158 in upper shoe 152 of body 150, such that the proximal face 157 of enlarged distal end 173 may apply a retraction force on upper shoe 152 when the drive cable 171 is pulled proximally. Drive rod 175 is operationally connected to an actuator which allows distal translation and proximal retraction of the actuation assembly. Those skilled in the art will recognize that in a manually actuated instrument, the actuator may be a movable handle, such as moveable handle 102b shown in FIG. 1; in a powered instrument the actuator may be a button (not shown) that causes a motor to act on the drive rod; and in a robotic system, the actuator may be a control device such as the control devices described below in connection with FIGS. 11 and 12.

During actuation of illustrative surgical instrument 100, drive rod 175 applies force to coil 120, thereby causing coil 120 to apply force to upper shoe 152 of drive member 150, translating it distally initially closing jaws 111, 112 and then ejecting staples 124 from cartridge 122 to staple tissue. After stapling is complete, drive rod 175 applies a force in the proximal direction to effect retraction of drive member. During retraction, enlarged distal end 173 of drive cable 171 is obstructed by wall 157 of enlarged portion 159 of bore 158, causing drive cable 171 to apply force to upper shoe 152 of drive member 150, thereby translating drive member 150 in the proximal direction. One of ordinary skill in the art will appreciate that drive member 150, drive cable 171, and drive rod 175 all move in unison and remain in the same relative position to each other.

Figure 10:
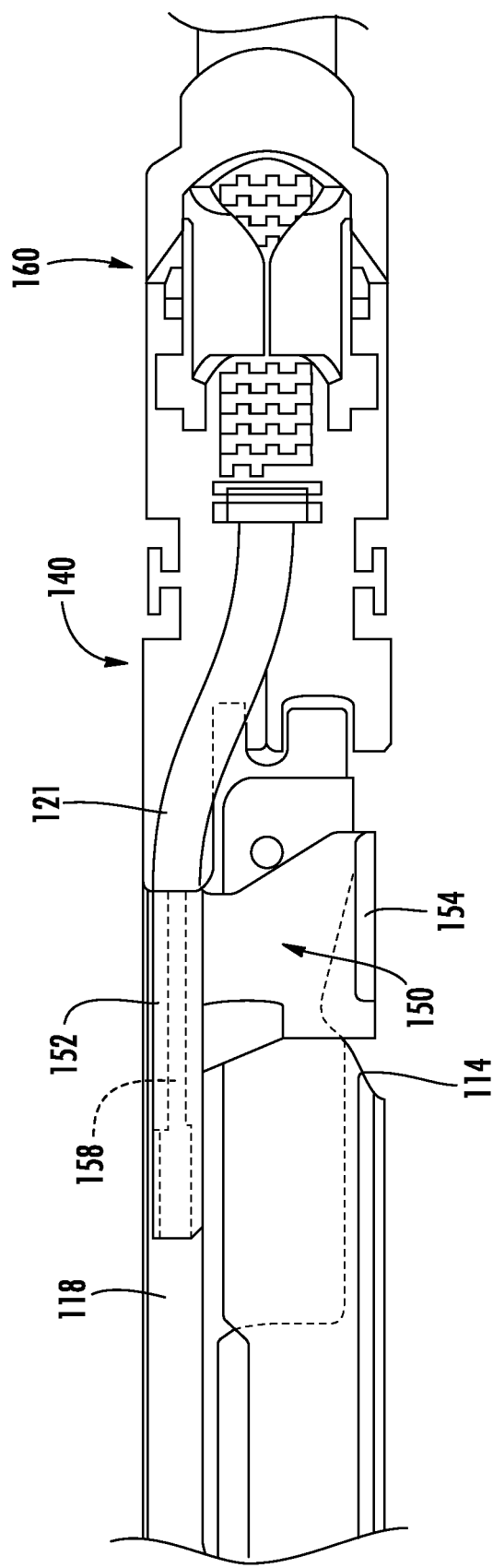
FIG. 10 is a cross-sectional side view of the end portion of the illustrative surgical instrument of FIG. 1.

Referring now to FIG. 10, in use, drive member 150 is positioned proximally of cam surface 114 formed on movable jaw 112. As drive member 150 translates in the distal direction, movable jaw 112 will rotate towards the closed position around a pivot pin 130 (see, for example, FIGS. 1A and 1D). Once drive member 150 has come into contact with cam surface 114 of movable jaw 112, lower portion 154 of drive member 150 rides underneath cam surface 114, drive member 150 pushes movable jaw 112, causing it to pivot towards the closed position. In the closed position, drive member 150 has translated distally past cam surface 114. In this position, tissue is clamped, and further advancement of the drive member will sever and staple tissue.

Figure 11:
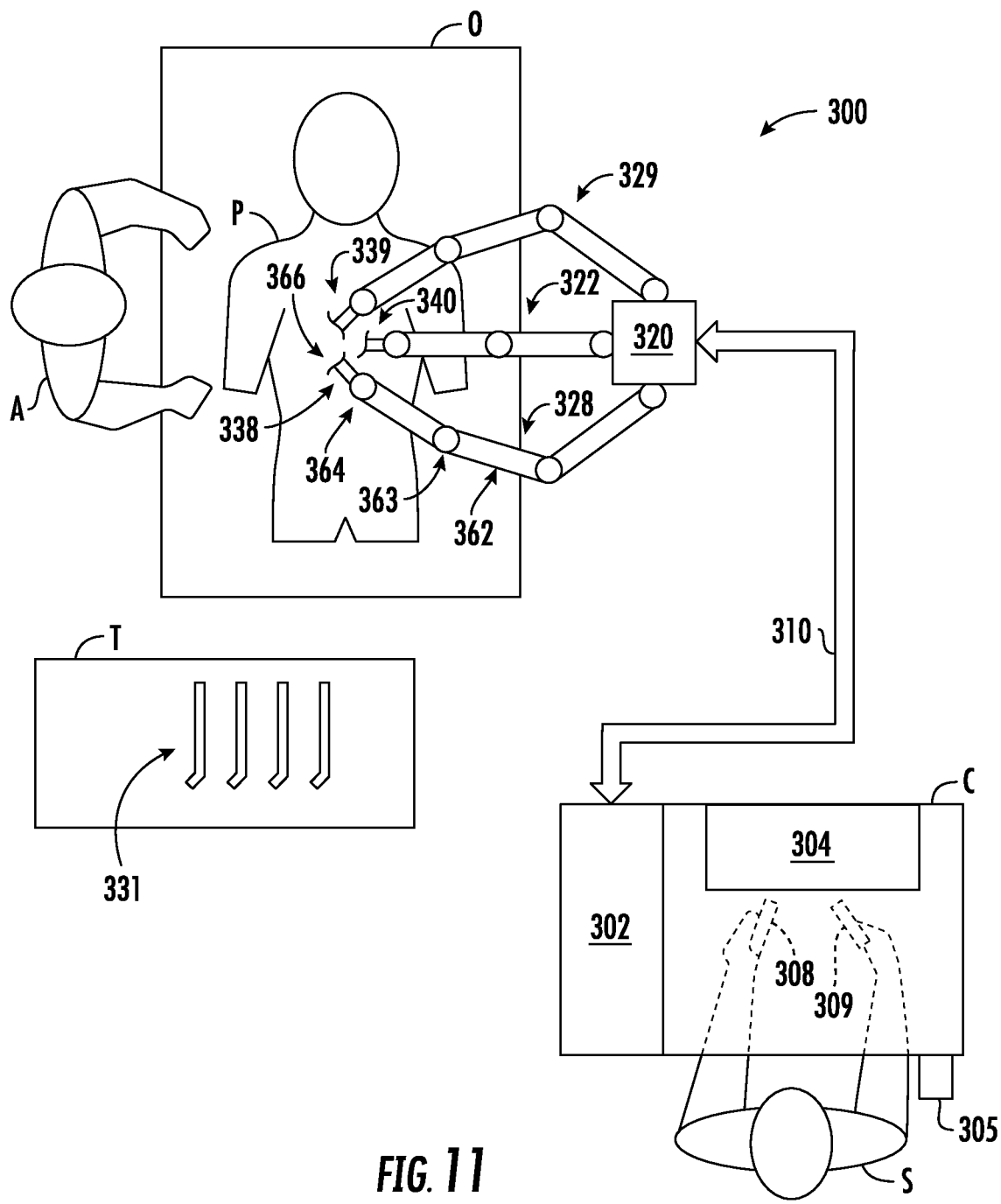
FIG. 11 illustrates a top view of an operating room employing a robotic surgical system utilizing aspects of the present invention.

FIG. 11 illustrates, as an example, a top view of an operating room employing a robotic surgical system. The robotic surgical system in this case is a robotic surgical system 300 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a monitor 304 for displaying an image of a surgical site to the Surgeon, left and right manipulatable control devices 308 and 309, a foot pedal 305, and a processor 302. The control devices 308 and 309 may include any one or more of a variety of input devices such as joysticks, gloves, trigger-guns, hand-operated controllers, or the like. The processor 302 may be a dedicated computer that may be integrated into the Console or positioned next to it.

The Surgeon performs a minimally invasive surgical procedure by manipulating the control devices 308 and 309 (also referred to herein as "master manipulators") so that the processor 302 causes their respectively associated robotic arm assemblies, 328 and 329, (also referred to herein as "slave manipulators") to manipulate their respective removably coupled surgical instruments 338 and 339 (also referred to herein as "tools") accordingly, while the Surgeon views the surgical site in 3-D on the Console monitor 304 as it is captured by a stereoscopic endoscope 340.

Each of the tools 338 and 339, as well as the endoscope 340, may be inserted through a cannula or other tool guide (not shown) into the Patient so as to extend down to the surgical site through a corresponding minimally invasive incision such as incision 366. Each of the robotic arms is conventionally formed of links, such as link 362, which are coupled together and manipulated through motor controlled or active joints, such as joint 363.

The number of surgical tools used at one time and consequently, the number of robotic arms being used in the system 300 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 331 from a Tray ("T") in the operating room.

The monitor 304 may be positioned near the Surgeon's hands so that it will display a projected image that is oriented so that the Surgeon feels that he or she is actually looking directly down onto the operating site. To that end, images of the tools 338 and 339 may appear to be located substantially where the Surgeon's hands are located.

The processor 302 performs various functions in the system 300. One important function that it performs is to translate and transfer the mechanical motion of control devices 308 and 309 to their respective robotic arms 328 and 329 through control signals over bus 310 so that the Surgeon can effectively manipulate their respective tools 338 and 339. Another important function is to implement various control system processes as described herein.

Although described as a processor, it is to be appreciated that the processor 302 may be implemented in practice by any combination of hardware, software and firmware. Also, its functions as described herein may be performed by one unit, or divided up among different components, each of which may be implemented in turn by any combination of hardware, software and firmware. For additional details on robotic surgical systems, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are hereby incorporated herein by reference in their entirety for all purposes.

Figure 12:
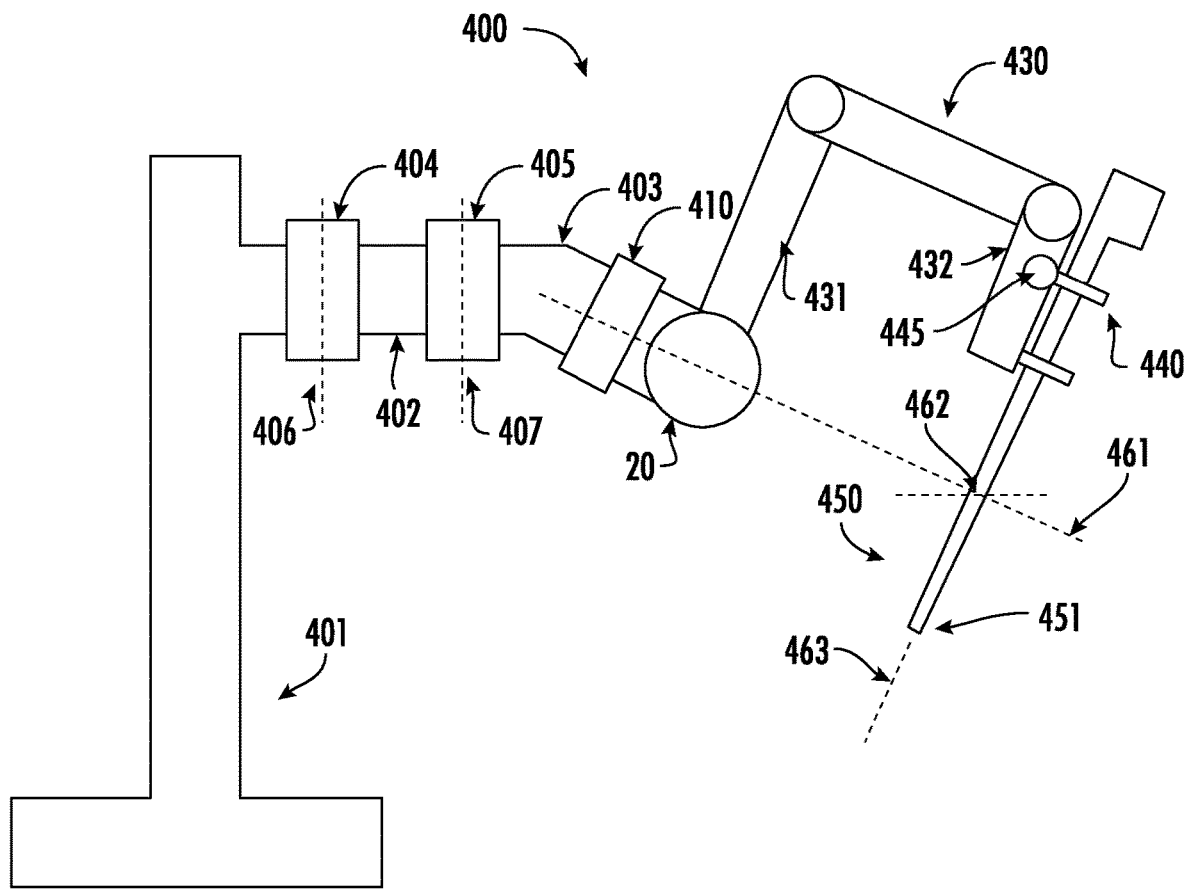
FIG. 12 illustrates a simplified side view of a robotic arm assembly that is usable with various aspects of the present invention.

FIG. 12 illustrates, as an example, a side view of a simplified (not necessarily in proportion or complete) illustrative robotic arm assembly 400 (which is representative of robotic arm assemblies 328 and 329) holding a surgical instrument 450 (which is representative of tools 338 and 339) for performing a surgical procedure. The surgical instrument 450 is removably held in tool holder 440. The arm assembly 400 is mechanically supported by a base 401, which may be part of a patient-side movable cart or affixed to the operating table or ceiling. It includes links 402 and 403, which are coupled together and to the base 401 through setup joints 404 and 405.

The setup joints 404 and 405 in this example are passive joints that allow manual positioning of the arm 400 when their brakes are released. For example, setup joint 404 allows link 402 to be manually rotated about axis 406, and setup joint 405 allows link 403 to be manually rotated about axis 407. Although only two links and two setup joints are shown in this example, more or less of each may be used as appropriate in this and other robotic arm assemblies in conjunction with the present invention. For example, although setup joints 404 and 405 are useful for horizontal positioning of the arm 400, additional setup joints may be included and useful for limited vertical and angular positioning of the arm 400. For major vertical positioning of the arm 400, however, the arm 400 may also be slidably moved along the vertical axis of the base 401 and locked in position.

The robotic arm assembly 400 also includes three active joints driven by motors. A yaw joint 410 allows arm section 430 to rotate around an axis 461, and a pitch joint 420 allows arm section 430 to rotate about an axis perpendicular to that of axis 461 and orthogonal to the plane of the drawing. The arm section 430 is configured so that sections 431 and 432 are always parallel to each other as the pitch joint 420 is rotated by its motor. As a consequence, the instrument 450 may be controllably moved by driving the yaw and pitch motors so as to pivot about the pivot point 462, which is generally located through manual positioning of the setup joints 404 and 405 so as to be at the point of incision into the patient. In addition, an insertion gear 445 may be coupled to a linear drive mechanism (not shown) to extend or retract the instrument 450 along its axis 463.

Although each of the yaw, pitch and insertion joints or gears, 410, 420 and 445, is controlled by an individual joint or gear controller, the three controllers are controlled by a common master/slave control system so that the robotic arm assembly 400 (also referred to herein as a "slave manipulator") may be controlled through user (e.g., surgeon) manipulation of its associated master manipulator. A more complete description of illustrative robotic surgical systems for use with the present invention can be found in commonly-assigned U.S. Pat. Nos. 9,295,524, 9,339,344, 9,358,074, and 9,452,019, the complete disclosures of which are hereby incorporated by reference in their entirety for all purposes.

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

While several embodiments have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

The invention claimed is:

1. A surgical instrument comprising:
a cartridge comprising one or more staple pushers each having a body and a drive rod pivotally coupled to the body;
an end effector having first and second jaws movable between open and closed positions, wherein at least one of the jaws includes a channel for receiving the cartridge with one or more staples, the channel having a height substantially perpendicular to a longitudinal axis of the end effector; and
a drive member comprising a main body with a projection extending laterally outward from the main body, the drive member being configured to engage the staples and drive the staples in a direction transverse to the longitudinal axis as the drive member is translated longitudinally through the end effector, wherein the projection has a height substantially less than the height of the channel and wherein the drive rod has a proximal end configured for receiving the projection on the drive member.

2. The surgical instrument of claim 1, wherein distal translation of the drive member causes the drive rod to pivot relative to the staple pusher and drive the staple pusher in a substantially perpendicular direction to the longitudinal axis of the staple cartridge.

3. The surgical instrument of claim 1, wherein the main body of the drive member comprises top and bottom surfaces and a side surface, wherein the projection comprises a fin extending laterally outward from the side surface, wherein a height of the side surface is substantially larger than a height of the fin.

4. The surgical instrument of claim 3, wherein the main body comprises a second side surface opposite the side surface and a second fin extending laterally outward from the second side surface, wherein a height of the second side surface if substantially larger than a height of the second fin.

5. The surgical instrument of claim 1 further comprising an end effector having a first fixed jaw and a second jaw configured to move relative to the first jaw from an open position to a closed position, wherein the staple cartridge is coupled to one of the first or second jaws.

6. The surgical instrument of claim 5 further comprising:
an actuation mechanism in contact with the drive member and configured to translate the drive member distally through the end effector and retract the drive member proximally through the end effector; and
an actuator operatively connected to the actuation mechanism, wherein the actuator includes a control device of a robotic surgical system.

7. A surgical instrument comprising:
a staple cartridge comprising a housing containing a staple and a staple pusher, the housing having a longitudinal axis;
a drive rod pivotally coupled to the staple pusher;
a drive member configured to translate longitudinally through the housing and engage the drive rod to pivot the drive rod with respect to the staple pusher and advance the staple pusher in a direction transverse to the longitudinal axis of the housing; and
wherein the drive member comprises an elongate body and a projection extending laterally outward from said elongate body, said projection being configured to engage said drive rod.

8. The surgical instrument of claim 7 further comprising an end effector having a first fixed jaw and a second jaw configured to move relative to the first jaw from an open position to a closed position, wherein the staple cartridge is coupled to one of the first or second jaws.

9. The surgical instrument of claim 7 further comprising a hinge coupling the drive rod to the staple pusher, wherein distal translation of the drive member causes the drive rod to pivot about the hinge and translate the staple pusher in a substantially perpendicular direction to the longitudinal axis.

10. The surgical instrument of claim 9, wherein the drive rod comprises an elongate portion coupled to a curved portion and wherein the curved portion comprises the hinge.

11. The surgical instrument of claim 7, wherein the drive member has top and bottom surfaces and a side surface, wherein the projection comprises a fin extending laterally outward from the side surface, wherein a first height of the side surface is substantially larger than a second height of the fin.

12. The surgical instrument according to claim 7 further comprising:
an actuation mechanism in contact with the drive member and configured to translate the drive member distally through the end effector and retract the drive member proximally through the end effector; and
an actuator operatively connected to the actuation mechanism, wherein the actuator includes a control device of a robotic surgical system.

13. A staple cartridge for a surgical instrument comprising:
a staple support comprising an elongate body with a top surface configured for receiving a staple; and
a drive rod pivotally coupled to the staple support and configured to translate the staple support in a direction transverse to the elongate body, wherein the drive rod comprises an elongate portion coupled to a curved portion and wherein the curved portion is coupled to the elongate body of the staple support.

14. The staple cartridge of claim 13 further comprising a hinge pivotally coupling the drive rod to the staple support.

15. The staple cartridge of claim 14, wherein the hinge is integral with the drive rod.

16. The staple cartridge of claim 13, wherein the elongate portion has an end surface, wherein movement of the end surface in a first direction causes movement of the staple support in a second direction transverse to the first direction.

17. The staple cartridge of claim 16, wherein the staple support has a bottom surface and a height between the top and bottom surfaces, and wherein the elongate portion of the drive rod extends away from the staple support in a substantially longitudinal direction, said elongate portion having a length greater than the height of the staple support.

* * * * *